(12) United States Patent
O'Driscoll et al.

(10) Patent No.: US 7,608,110 B2
(45) Date of Patent: Oct. 27, 2009

(54) SYSTEMS FOR BONE REPLACEMENT

(76) Inventors: Shawn W. O'Driscoll, 2281 Hardwood Ct. SW., Rochester, MN (US) 55902; Joel Gillard, 6937 NE. Alameda St., Portland, OR (US) 97213; David G. Jensen, 555 SW. Fifteenth St., Troutdale, OR (US) 97060

( * ) Notice: Subject to any disclaimer, the term of this patent is extended or adjusted under 35 U.S.C. 154(b) by 342 days.

(21) Appl. No.: 11/078,068

(22) Filed: Mar. 11, 2005

(65) Prior Publication Data
US 2005/0216090 A1    Sep. 29, 2005

Related U.S. Application Data

(60) Provisional application No. 60/552,957, filed on Mar. 11, 2004, provisional application No. 60/571,008, filed on May 13, 2004.

(51) Int. Cl.
*A61F 2/38* (2006.01)
(52) U.S. Cl. ............... 623/20.11; 623/20.12; 623/20.13
(58) Field of Classification Search ............... 623/20.11, 623/20.12, 20.13
See application file for complete search history.

(56) References Cited

U.S. PATENT DOCUMENTS

| | | | |
|---|---|---|---|
| 807,473 A | 12/1905 | Kolar et al. | |
| 2,696,817 A | 12/1954 | Prevo | |
| 3,103,926 A | 9/1963 | Cochran | |
| 3,656,186 A | 4/1972 | Dee | |
| 3,708,805 A | 1/1973 | Scales et al. | |
| 3,748,662 A | 7/1973 | Helfet | |
| 3,772,709 A | 11/1973 | Swanson | |
| 3,774,244 A | 11/1973 | Walker | |
| 3,816,854 A | 6/1974 | Schlein | |
| 3,852,831 A | 12/1974 | Dee | |
| 3,919,725 A | 11/1975 | Swanson et al. | |
| 3,939,496 A | 2/1976 | Ling et al. | |
| 3,990,117 A | 11/1976 | Pritchard et al. | |
| 4,000,525 A | 1/1977 | Klawitter et al. | |
| 4,007,494 A | 2/1977 | Sauer | |
| 4,008,495 A | 2/1977 | Cavendish et al. | |
| 4,021,864 A | 5/1977 | Waugh | |
| 4,034,418 A | 7/1977 | Jackson et al. | |
| 4,038,704 A | 8/1977 | Ring | |
| 4,057,858 A * | 11/1977 | Helfet | 623/20.11 |
| 4,059,854 A | 11/1977 | Laure | |
| 4,079,469 A | 3/1978 | Wadsworth | |
| 4,085,466 A | 4/1978 | Goodfellow et al. | |

(Continued)

FOREIGN PATENT DOCUMENTS

WO    2005/020851    3/2005

(Continued)

OTHER PUBLICATIONS

Sulzer Medica, Sulzer Orthopedics Joint Care/Fracture Care Anatomical Shoulder Product Guide, 2000.

(Continued)

*Primary Examiner*—David H Willse
*Assistant Examiner*—Javier G Blanco
(74) *Attorney, Agent, or Firm*—Kolisch Hartwell, PC

(57) ABSTRACT

Systems for replacement of the ends of bones with prostheses, and methods of using the systems for bone replacement.

13 Claims, 8 Drawing Sheets

U.S. PATENT DOCUMENTS

| | | | |
|---|---|---|---|
| 4,106,130 A | 8/1978 | Scales | |
| 4,129,902 A | 12/1978 | Harmon | |
| 4,131,956 A | 1/1979 | Treace | |
| 4,166,292 A | 9/1979 | Bokros | |
| 4,187,559 A | 2/1980 | Grell et al. | |
| 4,206,517 A | 6/1980 | Pappas et al. | |
| 4,224,695 A | 9/1980 | Grundei et al. | |
| 4,242,758 A * | 1/1981 | Amis et al. | 623/20.11 |
| 4,259,072 A | 3/1981 | Hirabayashi et al. | |
| 4,280,231 A | 7/1981 | Swanson | |
| 4,285,070 A | 8/1981 | Averill | |
| 4,293,963 A | 10/1981 | Gold et al. | |
| 4,301,552 A | 11/1981 | London | |
| 4,378,607 A | 4/1983 | Wadsworth | |
| 4,383,337 A | 5/1983 | Volz et al. | |
| 4,384,373 A | 5/1983 | Sivash | |
| 4,502,160 A | 3/1985 | Moore et al. | |
| 4,521,924 A | 6/1985 | Jacobsen et al. | |
| 4,538,306 A | 9/1985 | Dorre et al. | |
| 4,550,450 A | 11/1985 | Kinnett | |
| 4,553,273 A | 11/1985 | Wu | |
| 4,728,332 A | 3/1988 | Albrektsson | |
| 4,743,261 A | 5/1988 | Epinette | |
| 4,822,364 A | 4/1989 | Inglis et al. | |
| 4,892,546 A | 1/1990 | Kotz et al. | |
| 4,919,671 A | 4/1990 | Karpf | |
| 4,963,153 A | 10/1990 | Noesberger et al. | |
| 5,030,237 A | 7/1991 | Sorbie et al. | |
| 5,037,439 A | 8/1991 | Albrektsson et al. | |
| 5,047,057 A * | 9/1991 | Lawes | 623/20.29 |
| 5,092,895 A | 3/1992 | Albrektsson et al. | |
| 5,108,441 A | 4/1992 | McDowell | |
| 5,133,760 A | 7/1992 | Petersen et al. | |
| 5,152,797 A | 10/1992 | Luckman | |
| 5,314,484 A | 5/1994 | Huene | |
| 5,360,450 A | 11/1994 | Giannini | |
| 5,373,621 A | 12/1994 | Ducheyne et al. | |
| 5,376,121 A | 12/1994 | Huene et al. | |
| 5,462,563 A | 10/1995 | Shearer et al. | |
| 5,507,817 A | 4/1996 | Craig et al. | |
| 5,571,196 A | 11/1996 | Stein | |
| 5,593,449 A | 1/1997 | Roberson, Jr. | |
| 5,702,466 A | 12/1997 | Pappas et al. | |
| 5,702,470 A | 12/1997 | Menon | |
| 5,702,479 A * | 12/1997 | Schawalder | 623/23.15 |
| 5,702,480 A | 12/1997 | Kropf et al. | |
| 5,723,015 A | 3/1998 | Risung et al. | |
| 5,725,586 A | 3/1998 | Sommerich | |
| 5,782,920 A | 7/1998 | Colleran | |
| 5,782,922 A * | 7/1998 | Vandewalle | 606/87 |
| 5,782,923 A | 7/1998 | Engelbrecht et al. | |
| 5,824,096 A | 10/1998 | Pappas et al. | |
| 5,827,285 A | 10/1998 | Bramlet | |
| 5,879,389 A | 3/1999 | Koshino | |
| 5,879,395 A * | 3/1999 | Tornier et al. | 623/20.13 |
| 5,944,756 A | 8/1999 | Fischetti et al. | |
| 5,984,969 A | 11/1999 | Matthews et al. | |
| 6,022,352 A | 2/2000 | Vandewalle | |
| 6,027,534 A | 2/2000 | Wack et al. | |
| 6,051,751 A | 4/2000 | Sioshansi et al. | |
| 6,149,687 A | 11/2000 | Gray, Jr. et al. | |
| 6,162,253 A | 12/2000 | Conzemius et al. | |
| 6,165,221 A | 12/2000 | Schmotzer | |
| 6,168,630 B1 * | 1/2001 | Keller et al. | 623/21.11 |
| 6,203,575 B1 | 3/2001 | Farey | |
| 6,217,616 B1 * | 4/2001 | Ogilvie | 623/20.11 |
| 6,270,529 B1 | 8/2001 | Terrill-Grisoni et al. | |
| 6,290,725 B1 | 9/2001 | Weiss et al. | |
| 6,306,171 B1 | 10/2001 | Conzemius | |
| 6,306,174 B1 | 10/2001 | Gie et al. | |
| 6,321,606 B1 | 11/2001 | Ishii et al. | |
| 6,342,075 B1 | 1/2002 | MacArthur | |
| 6,358,283 B1 | 3/2002 | Hogfors et al. | |
| 6,361,563 B2 | 3/2002 | Terrill-Grisoni et al. | |
| 6,379,387 B1 * | 4/2002 | Tornier | 623/20.12 |
| 6,436,137 B2 | 8/2002 | Wang et al. | |
| 6,494,914 B2 | 12/2002 | Brown et al. | |
| 6,503,280 B2 | 1/2003 | Repicci | |
| 6,520,964 B2 | 2/2003 | Tallarida et al. | |
| 6,554,838 B2 | 4/2003 | McGovern et al. | |
| 6,569,203 B1 | 5/2003 | Keller | |
| 6,656,225 B2 | 12/2003 | Martin | |
| 6,699,290 B1 | 3/2004 | Wack et al. | |
| 6,709,459 B1 | 3/2004 | Cooney, III et al. | |
| 6,716,248 B2 | 4/2004 | Huene | |
| 6,767,368 B2 | 7/2004 | Tornier | |
| 6,774,155 B2 | 8/2004 | Martakos et al. | |
| 6,800,670 B2 | 10/2004 | Shen et al. | |
| 6,818,020 B2 | 11/2004 | Sun et al. | |
| 6,890,357 B2 | 5/2005 | Tornier | |
| 6,997,957 B2 | 2/2006 | Huene | |
| 7,160,329 B2 | 1/2007 | Cooney, III et al. | |
| 7,247,170 B2 | 7/2007 | Graham et al. | |
| 7,384,430 B2 | 6/2008 | Greer et al. | |
| 7,419,507 B2 | 9/2008 | Cook et al. | |
| 7,449,028 B2 | 11/2008 | Ball | |
| 2001/0037154 A1 | 11/2001 | Martin | |
| 2002/0120339 A1 * | 8/2002 | Callaway et al. | 623/19.14 |
| 2003/0040805 A1 | 2/2003 | Minamikawa | |
| 2003/0212457 A1 | 11/2003 | Martin | |
| 2003/0225413 A1 | 12/2003 | Sanford et al. | |
| 2004/0186580 A1 | 9/2004 | Steinmann | |
| 2004/0193278 A1 * | 9/2004 | Maroney et al. | 623/19.14 |
| 2005/0049710 A1 | 3/2005 | O'Driscoll | |
| 2005/0216090 A1 | 9/2005 | O'Driscoll et al. | |
| 2006/0004462 A1 * | 1/2006 | Gupta | 623/21.13 |
| 2006/0052725 A1 | 3/2006 | Santilli | |
| 2007/0073409 A1 | 3/2007 | Cooney, III et al. | |
| 2008/0195217 A1 | 8/2008 | Scheker | |
| 2008/0288079 A1 | 11/2008 | Leibel | |

FOREIGN PATENT DOCUMENTS

| WO | 2005/086939 | 9/2005 |
|---|---|---|

OTHER PUBLICATIONS

Sulzer Medica, Sulzer Orthopedics Joint and Fracture Care Anatomical Shoulder Flyer, 2000.

Swanson Radial Head Implant Product Information, Jan. 29, 2003.

Ushio, *The Journal of Bone & Joint Surgery*, M. Partial hemiarthroplasty for the treatment of osteonecrosis of the femoral head, 2003.

Biomet Orthopedics, Inc., Explor Modular Radial Head Surgical Technique, Mar. 2004.

Kmi, Katalyst Bipolar Radial Head System Brochure, no date provided.

Rayhack Osteotomy Systems, Ulnar Shortening Summary, no date provided.

\* cited by examiner

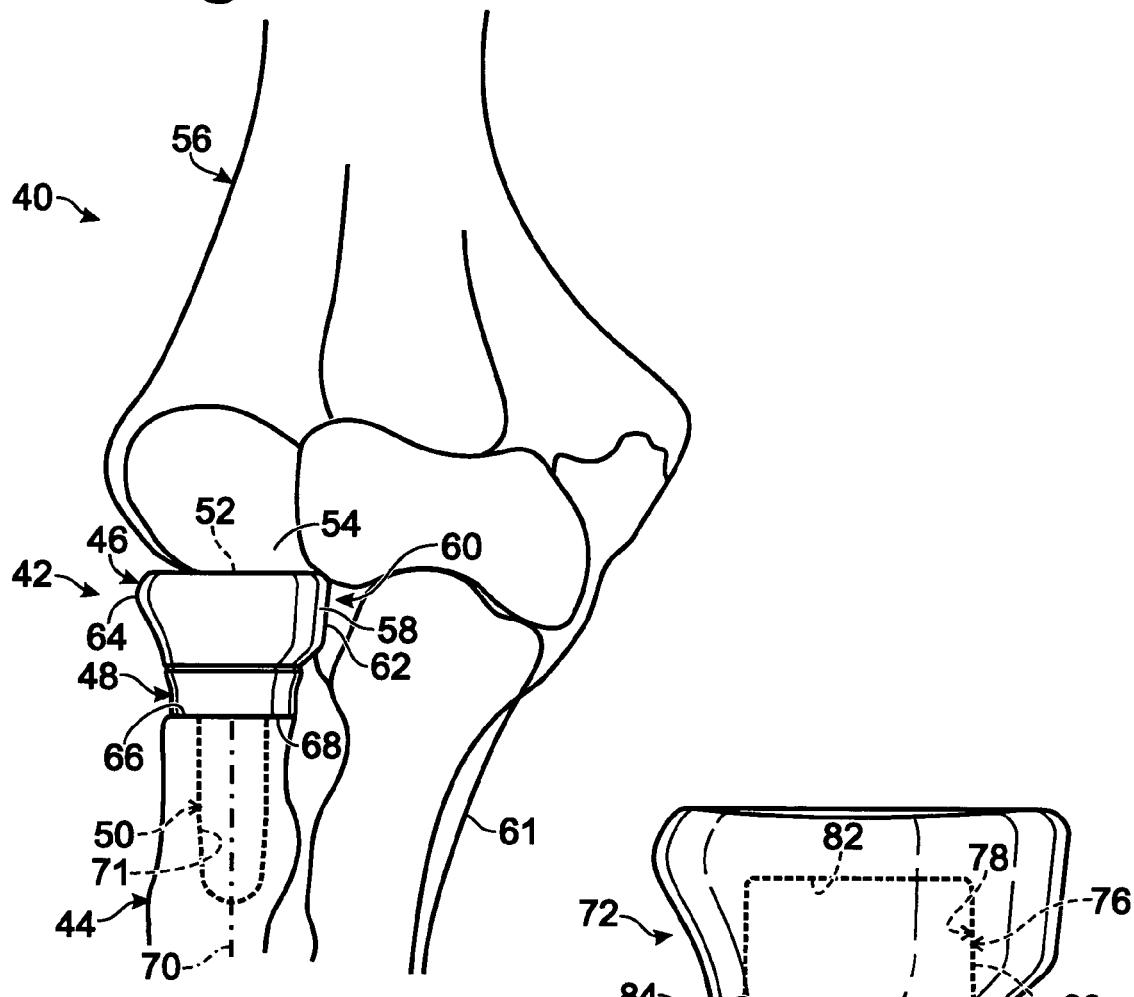
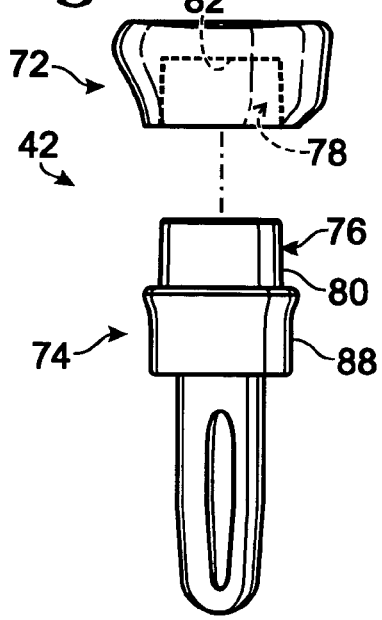
Fig. 1
Fig. 2
Fig. 3

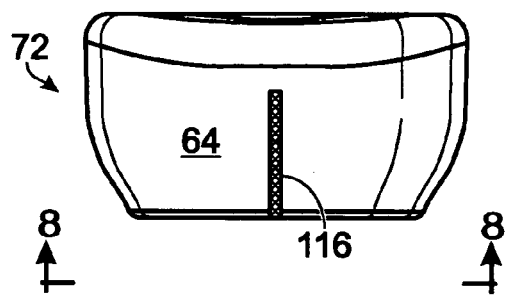
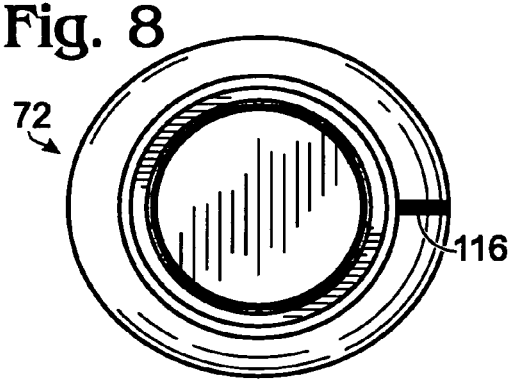
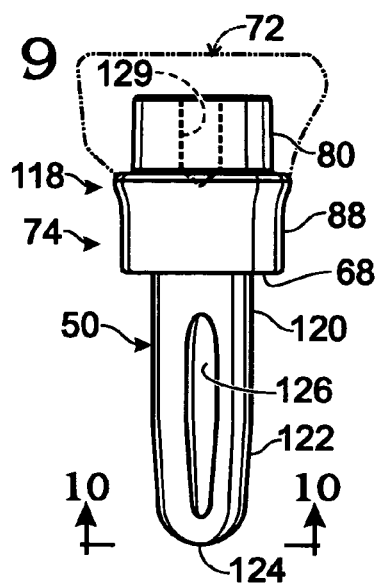
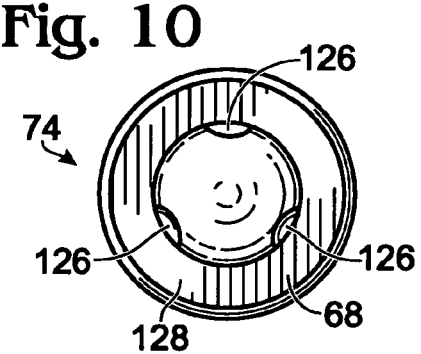
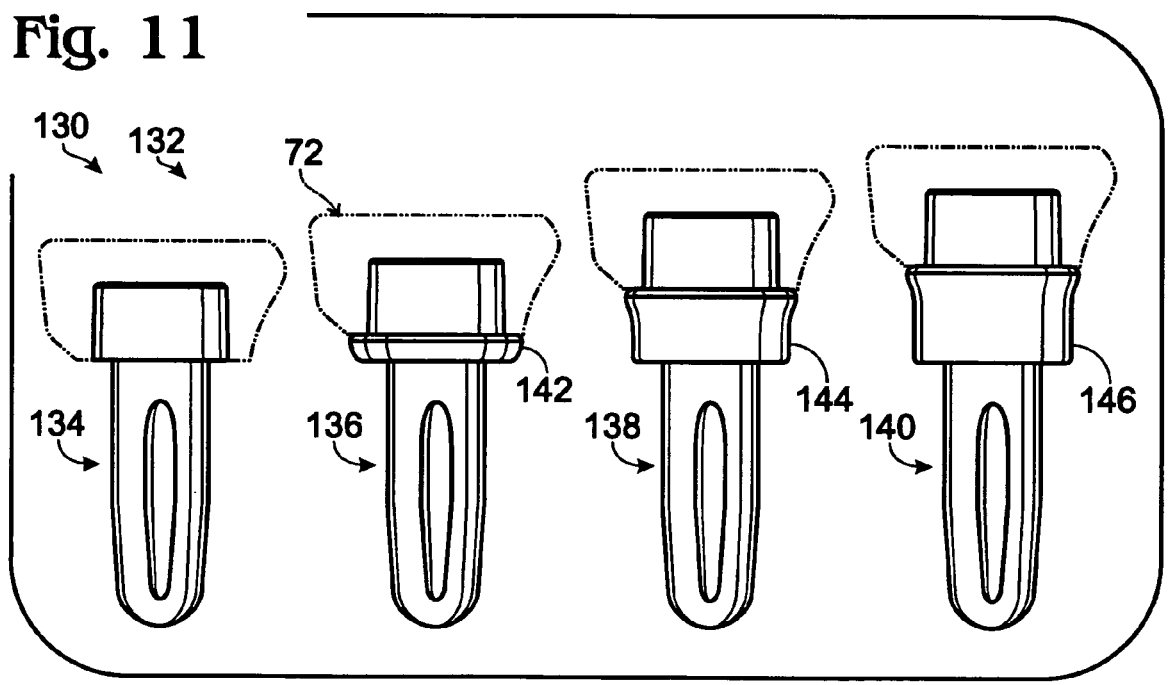

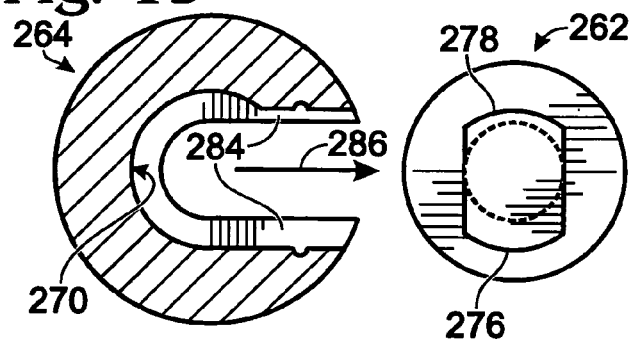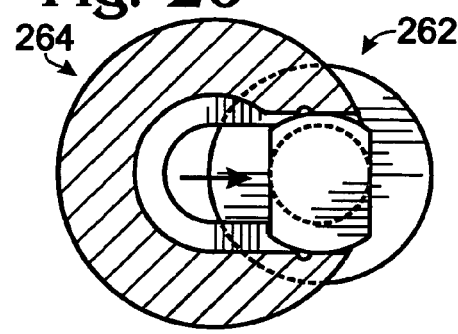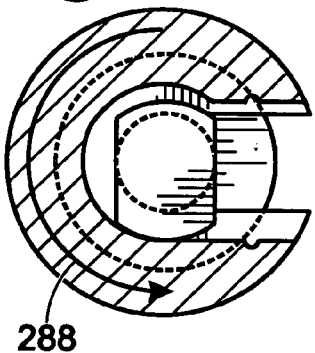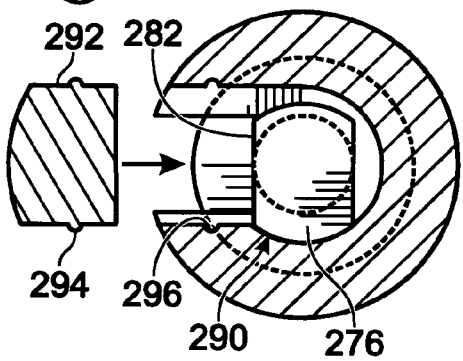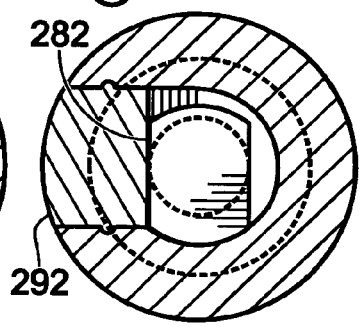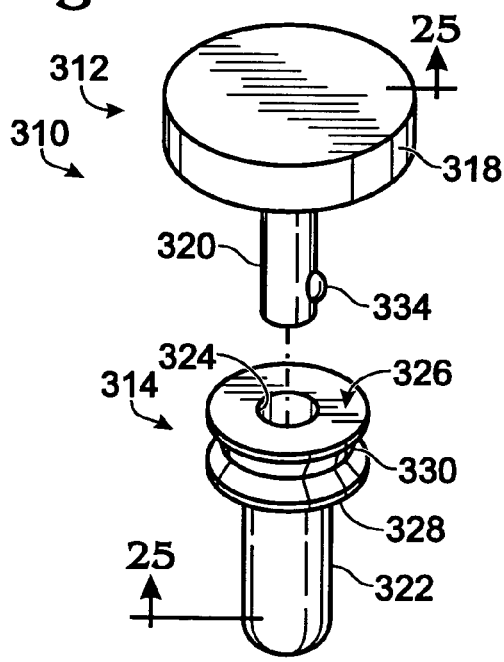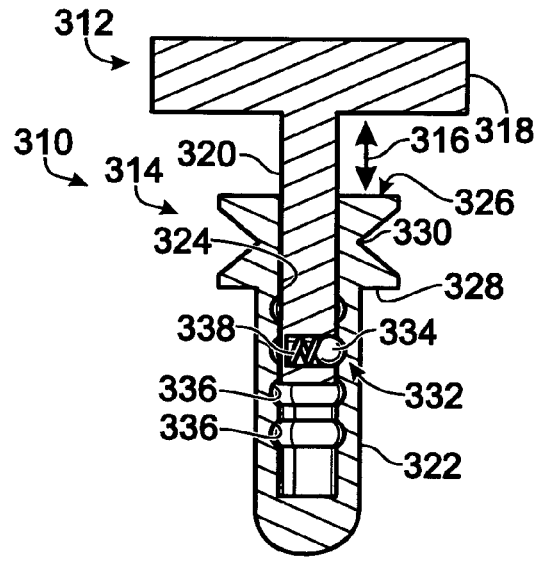

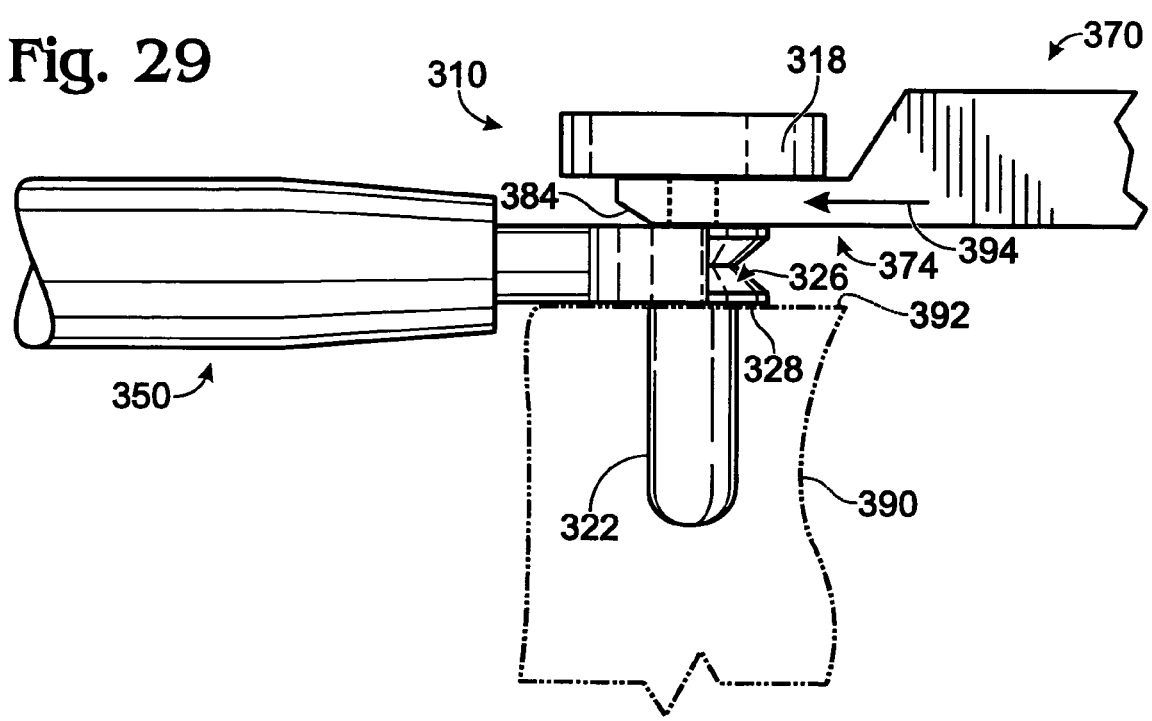

SYSTEMS FOR BONE REPLACEMENT

CROSS-REFERENCES TO PRIORITY APPLICATIONS

This application is based upon and claims the benefit under 35 U.S.C. § 119(e) of the following U.S. provisional patent applications: Ser. No. 60/552,957, filed Mar. 11, 2004; and Ser. No. 60/571,008, filed May 13, 2004. Each of these provisional patent applications is incorporated herein by reference in its entirety for all purposes.

BACKGROUND

The human skeleton is composed of 206 individual bones that perform a variety of important functions, including support, movement, protection, storage of minerals, and formation of blood cells. To ensure that the skeleton retains its ability to perform these important functions, and to reduce pain and disfigurement, fractured bones should be repaired promptly and properly. External or internal fixation devices (such as casts, bone plates, or nails, among others) may be used on less severe fractures that are reconstructable, to reinforce fractured bones and keep them aligned during healing. However, more severe fractures (or disease), particularly near the end of a bone, may damage the bone sufficiently to preclude reconstruction by fixation only. In these cases, a bone prosthesis may be installed to replace bone, for example, to provide an artificial joint or a portion thereof.

The elbow joint provides an exemplary site of prosthesis installation. The elbow joint is formed at the intersection of the humerus, radius, and ulna bones. In this joint, the radius plays a dual role by movement about two axes so that the elbow can operate as a hinge joint and the forearm can pronate and supinate. To guide and restrict this movement about two axes, the head of the radius (the radial head) includes (1) a concave axial surface for articulation with the capitellum of the humerus and (2) a convex side surface for articulation with the radial notch of the ulna.

Trauma to the elbow joint often involves damage to the radial head. With such trauma, replacement of the radial head with a corresponding prosthesis may help restore the function of the elbow joint. However, this prosthesis may be difficult to install for proper articulation with the ulna and/or humerus.

SUMMARY

The present teachings provide systems for replacement of the ends of bones with prostheses, and methods of using the systems for bone replacement.

BRIEF DESCRIPTION OF THE DRAWINGS

FIG. 1 is an anterior view of a right elbow joint including an exemplary radial head prosthesis installed in the radius bone in place of the natural head of the radius, in accordance with aspects of the present teachings.

FIG. 2 is a side elevation view of the radial head prosthesis of FIG. 1, taken from the anterior side of the prosthesis in the absence of bone, in accordance with aspects of the present teachings.

FIG. 3 is an exploded view of the radial head prosthesis of FIG. 2, in accordance with aspects of the present teachings.

FIG. 7 is a side elevation view of the head component of FIG. 4, taken generally along line 7-7 of FIG. 4.

FIG. 8 is a bottom view of the head component of FIG. 4.

FIG. 9 is a side elevation view of a body component of the radial head prosthesis of FIG. 2, in accordance with aspects of the present teachings.

FIG. 10 is a bottom view of the body component of FIG. 9, taken generally along line 10-10 of FIG. 9.

FIG. 11 is an exemplary set of body components that position a head component at different heights above a stem of the body components, in accordance with aspects of the present teachings.

FIG. 19 is a sectional view of the radial head prosthesis of FIG. 17, taken generally along line 19-19 of FIG. 18, with body and head components aligned for mating, in accordance with aspects of the present teachings.

FIGS. 20-23 are sectional views of the radial head prosthesis of FIG. 17, taken generally as in FIG. 19, with the body and head components positioned at various stages of assembly.

FIG. 24 is an exploded view of an exemplary trial prosthesis that may be included in the systems of the present teachings.

FIG. 25 is a sectional view of the exemplary trial prosthesis of FIG. 24, taken generally along line 25-25 of FIG. 24 with the prosthesis in an assembled configuration.

FIG. 29 is a side elevation view of the trial prosthesis and holder of FIG. 26, with the spacer tool of FIG. 28 inserted between head and body components of the trial prosthesis to adjust and/or measure the spacing of these components for selection of a corresponding implant prosthesis, in accordance with aspects of the present teachings.

DETAILED DESCRIPTION

Figure 4:
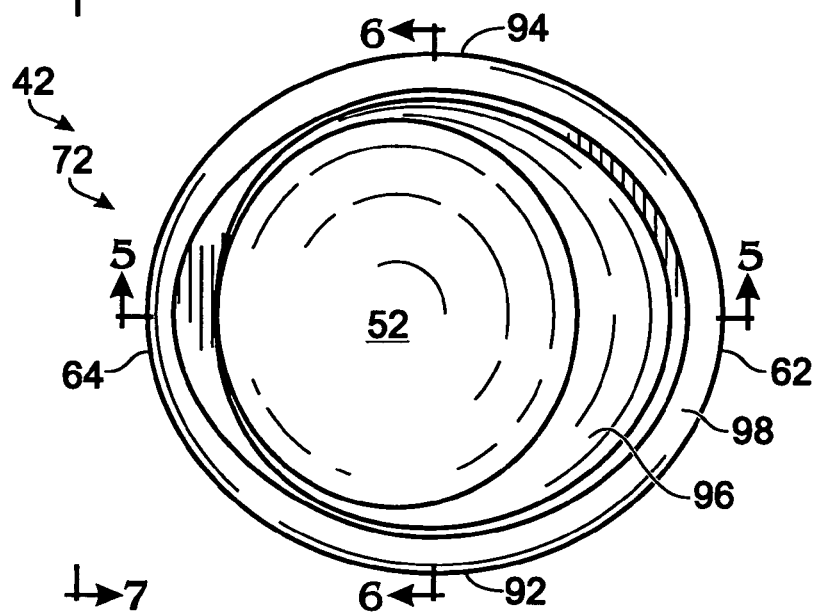
FIG. 4 is a plan view of a head component of the radial head prosthesis of FIG. 2, in accordance with aspects of the present teachings.

The present teachings provide systems for replacement of the ends (heads) of bones with prostheses, and methods of using the systems for bone replacement. The prostheses may be configured to replace the end(s) of any suitable bones, such as a proximal head of a radius bone, among others. The prostheses may have a unitary or a modular construction, to provide a head and a body with a stem. If modular, the prostheses may be formed by distinct head and body components, which may be assembled and/or mated by any suitable relative motion, such as axial motion, transverse motion, and/or rotation, among others, to mount a head of each prosthesis on a corresponding body. In some examples, the head may be tilted relative to the body. In some examples, a head component of the prosthesis may have an asymmetrical profile when viewed from anterior and posterior sides and/or from medial and lateral sides of the head component.

The body component (or body portion) may include various structures. The body component may include a stem sized to be received in a bore of the bone. In addition, the body component may include a mating structure for mounting the head component on the body component. Furthermore, in some examples, the body component may include an external spacer structure, such as a collar. The collar may have a characteristic dimension (e.g., length measured parallel to the long axis of the stem) that determines the spacing between the stem and the head component. (A characteristic dimension includes any dimension that describes a structure, such as length, width, diameter, thickness, height, radius, circumference, etc.). The collar also generally may replicate the structure of a missing neck region of the bone, and/or may include a shoulder to restrict entry of the prosthesis into bone.

In some examples, the systems may provide kits and/or trial prostheses. The kits may include one or more body components and/or one or more head components. The body components may have a different spacing between the stem and mating structure, a different stem diameter, a different stem length, and/or the like. Alternatively, or in addition, the head components may have different diameters, angular tilts, shapes, etc. Accordingly, the kits may permit selection of a suitable head-stem combination (and spacing) based on a recipient's anatomy and on the position and length of missing bone, to provide proper placement of the stem and proper articulation with an adjacent bone(s). In some cases, a trial prosthesis may be used to facilitate selection. The trial prosthesis may be continuously adjustable and/or selectively adjustable to predefined head-stem spacings (head heights) that correspond to the head-stem spacings of nontrial ("implant") prostheses in the kit. Overall, the systems of the present teachings may provide prostheses that are easier to install, fit better into joints, and/or have improved articulation with adjacent bones.

FIG. 1 shows a right elbow joint 40 including an exemplary radial head prosthesis 42 secured to the radius bone 44 in place of the natural proximal head of the radius. Radial head prosthesis 42 may include a head 46, a neck 48, and a stem 50.

The head may be shaped to articulate with adjacent bones in the elbow joint. The head may be orthogonal to the stem or may be tilted (see FIGS. 12-14). The head may have a proximal articulation surface 52 for articulation with the capitellum 54 of the humerus 56. In addition, the head (and/or a head component, see below) may have a side wall 58 for articulation with the radial notch 60 of ulna 61. The head may be radially symmetrical or asymmetrical, as shown here. Accordingly, an articulating, medial surface region 62 of the side wall may be shaped differently than a non-articulating, lateral surface region 64 of the side wall. For example, a medial side of the head (and/or head component) may have a substantially linear profile (a profile substantially formed by one or more line segments), and a lateral side of the head (and/or head component) may have a substantially curved (arcuate) profile. These distinct profiles may facilitate orienting the head (and/or head component) during installation (e.g., by visual or instrument-assisted inspection (such as with a fluoroscope)). In addition, a curved lateral profile may reduce soft tissue irritation or damage and may transition distally to a concave surface for engaging the annular ligament.

The neck may be a narrowed region of the prosthesis distal to the head. The neck may provide a smooth transition or contour from the head, and, optionally, to external radial surfaces circumscribing a cut or broken end surface 66 of the radius. Accordingly, the neck may taper distally from the head and may have a diameter or width that approximates the radial diameter or width measured at radial end surface 66. The neck also may define a shoulder or flange 68 immediately proximal to stem 50, to abut radial end surface 66 and thus restrict entry of the prosthesis into bone.

The stem may be a further narrowed region of the prosthesis distal to the neck. The stem may define a long axis 70 of the prosthesis and may be sized to be received in a bore 71 in the radius. The bore may be, for example, the medullary canal of the radius, which may be reamed or widened otherwise to accommodate the stem.

FIGS. 2 and 3 show a head component 72 and a body component 74 of the prosthesis. The head and body components may be configured so that the head component is assembled with the body component by axial (and/or transverse) motion relative to the body component. Accordingly, the head and body components may include a coupling mechanism defined by complementary mating structures 76, 78, such as a frustoconical projection 80 that fits into a complementary frustoconical cavity 82 (a Morris taper). When mated, the neck of the prosthesis may include a slight gap 84 formed between the distal end of the head component and a proximal ledge 86 of the body component (and also another gap between the proximal end of projection 80 and the proximal surface of cavity 82), to ensure that the head component is fully seated on the body component (see FIG. 2). The head component may form the head, a suitable portion (or all) of the neck, and, optionally, a shoulder that restricts entry of the prosthesis into the bore in bone. The body component may form the stem (an internal portion), and, optionally, the shoulder and the remainder of the neck (an external portion). Accordingly, the body component may have an external spacer region (or collar) 88 that positions mating structure 76 of the body component and thus determines the spacing ("height") of the head from the stem (and bone). Different body components may have spacer regions of different length (measured axially), to provide a surgeon with the ability to position the head at various distances from the stem (and the end of the bone). (The "height" of the head is defined by the distance of the head from the stem with the stem in a vertical disposition. This distance or spacing may be measured, for example, from the proximal or distal end of the head or head component to the proximal or distal end of the stem, among others.)

Further aspects of the present teachings are described in the following sections, including (I) general aspects of bone prostheses, (II) body portions, (III) head portions, (IV) coupling mechanisms, (V) kits, (VI) methods of installing bone prostheses, and (VII) examples.

I. GENERAL ASPECTS OF BONE PROSTHESES

Bone prostheses as described herein generally include any implant configured to replace at least a portion of a bone (or bones), and generally at least a portion of an end of a bone. Accordingly, the implant may replace a portion of, or all, subchondral (ossified) bone adjacent the end of the bone. In some examples, the implant also may replace a portion or all of an articulation surface of a joint, including cartilage that forms the articulation surface. In some examples, the implant may replace opposing articulation surfaces of a joint, such as by replacement of an anatomical joint with a mechanical joint.

The prostheses may be installed for any suitable purpose including treatment of injury or disease, among others. Accordingly, exemplary conditions for which the prostheses described herein may be indicated include fractures (breaks in bones), joint disease (such as arthritis), osteoporosis, osteotomies (cuts in bones), birth defects, cancer, and/or the like.

The prostheses described herein may be configured to replace any suitable portion of any suitable bone (or bones) of the human skeleton and/or of another vertebrate species. Exemplary bones for which the prostheses may be configured include bones of the arms (radius, ulna, humerus), legs (femur, tibia, fibula, patella), hands/wrists (e.g., phalanges, metacarpals, and carpals), feet/ankles (e.g., phalanges, metatarsals, and tarsals), vertebrae, scapulas, pelvic bones, cranial bones, ribs, and and/or clavicles, among others. Particular examples where bone prostheses may be suitable include, but are not limited to, proximal and distal metaphyseal regions of long bones, such as proximal or distal end regions of the humerus, the radius, the ulna, the tibia, and/or the femur, among others.

Each prosthesis may be configured to be installed in any suitable position relative to a bone. The prosthesis may be configured to be disposed as least partially internal to the bone, such as in a bore or canal defined by the bone. The bore may be at least partially engineered. Alternatively, or in addition, the bore may overlap and/or at least substantially correspond to a medullary canal of the bone. In some examples, the bore may be formed and/or accessed from external the bone by drilling, cutting, reaming, and/or injury, among others. The prosthesis also may be configured to be disposed at least partially external to the bone, for example, to provide an articulation surface and/or a site(s) for attachment of soft tissue and/or bone, and/or to space the articulation surface appropriately from a remaining portion of the bone, among others.

The prostheses may be formed of any suitable materials. Suitable materials for forming the prostheses may be biocompatible materials (such as metal alloys (titanium alloys, cobalt chromium alloys, stainless steel, etc.), composite materials, plastics (such as polyethylene, among others), ceramics, and/or the like), and/or bioabsorbable materials (such as polygalactic acid (PGA), polylactic acid (PLA), copolymers thereof, etc.), among others. The materials may be generally rigid to facilitate the ability of the prostheses to bear weight.

The prostheses may be configured to reduce irritation to the bone and surrounding tissue. For example, the prostheses may be formed of a biocompatible material, as described above. In addition, the prostheses may have rounded, burr-free surfaces to reduce irritation to tissue.

The prostheses described herein may be sized and shaped to replace particular portions of a bone (or bones). In use, the long axis of the prostheses (and/or a stem thereof) may be aligned with the long axis of the corresponding bone and/or may extend obliquely or transversely relative to the bone's long axis. The length and/or width of the prostheses may be varied according to the intended use, for example, to match the prostheses with a preselected region of bone(s) and/or a particular injury to the bone. In some embodiments, the prostheses may be configured for use on both sides of the body, such as when the prostheses are bilaterally symmetrical (having mirror-image symmetry). In some embodiments, the prostheses (e.g., prostheses with tilted heads) may be asymmetrical (lacking bilateral symmetry) and configured for use on either the left side or the right side of the body (and the skeleton thereof), but not both.

The prostheses may include any suitable surface contours, surface textures, and/or surface compositions. The surface contour of the head of the prosthesis may be configured to correspond to a surface contour of an articulation region that the head replaces. The surface texture of at least a portion of the prostheses may be smooth (with a relatively lower coefficient of friction), for example, to facilitate insertion of the stem into bone, assembly of the head and body components, and/or articulation with an opposing skeletal member(s), among others. Alternatively, or in addition, the prostheses may have porous and/or textured surfaces (with a relatively higher coefficient of friction), particularly on internal and/or external portions of the body component (and/or stem) and/or on a non-articulating surface region(s) of the head component, to promote, for example, bone ongrowth and/or ingrowth and or the ability attach the prostheses to bone with an adhesive. Alternatively, or in addition, the prostheses may include a distinct surface layer disposed on the body and/or head portions. The distinct surface layer may be, for example, a biopolymer, a synthetic polymer, an extracellular matrix, etc.

The prostheses may include one or more openings. The openings may be recesses, concavities, or through-holes, among others. The openings may be threaded or nonthreaded, and each prosthesis may include one or more threaded and/or nonthreaded openings. The openings may be configured for any suitable purpose, such as assembly of the head and body components (for example, an opening of one of the components that receives a generally complementary projection of the other of the components). Alternatively, or in addition, the openings may be configured to receive a rigid fastener (such as a pin, a screw, a staple, etc.), for example, as part of a detent mechanism configured to restrict uncoupling to the head and body components and/or to secure the head and/or body component to bone, among others. In some examples, a body component of the prostheses may include a threaded opening formed in a proximal surface of the body component. The threaded opening may receive a threaded tool to assist positioning the body component during installation, adjustment, or removal of the body component. In some examples, the openings may be configured to receive a flexible fastener, such as a suture or other nonrigid material to secure soft tissue and/or bone to the prostheses. Alternatively, or in addition, the head and/or body portions may include an axial bore/cannulation to permit, for example, placing the head and/or body portions over a guide wire.

The openings may have any suitable positions, sizes, and/or densities within each portion of a prosthesis. The openings may be arrayed generally in one or more lines in the body and/or head portions, for example, centered across the width of the body or head portion. Alternatively, the openings may be arranged nonlinearly, for example, disposed in an arcuate, staggered or other two-dimensional or three-dimensional arrangement. For example, the openings may include an angular offset and/or an axial offset to permit fasteners to be received in the openings from different directions and/or axial positions, such as to secure different bone fragments to the prosthesis.

The openings may have any suitable shape and structure. Exemplary shapes may include circular, elongate (such as elliptical, rectangular, oval), etc. The openings may be locking (threaded) or nonlocking (nonthreaded) and may include counterbores. The counterbores may be configured, for example, to receive a head of a bone screw, to reduce or eliminate protrusion of the head above an outer surface of the prosthesis. In some embodiments, the prostheses may include one or a plurality of elongate openings (slots) extending axially, obliquely, and/or transversely within the body (e.g., stem) and/or head portion of each prosthesis. The elongate openings may be used, for example, to adjust the position of the prostheses relative to bone, such as to permit dynamic positioning of the prostheses.

The prostheses may include one or more projections that extend above the general surface contour of the prosthesis. The projections may be ridges, tabs, and/or knobs, among others. For example, at least one of these projections may be a tab that defines one or more openings configured to receive rigid or flexible fasteners, as described above. Alternatively, or in addition, at least one of these projections may be configured as a stop or spacer structure that restricts movement of the prosthesis relative to bone or spaces the prosthesis from bone (such as to reduce friction and/or permit blood flow, among others). In some examples, the projections may include at least one sharp projection configured as a prong that penetrates bone to restrict movement of the prosthesis. In some examples, the projections may be included in coupling mechanisms by which head and body components of the prosthesis are assembled (see Section IV).

Further aspects of prostheses are described in the following patent and patent application, which are incorporated herein by reference: U.S. Pat. No. 6,494,913, issued Dec. 17, 2002; and U.S. patent application Ser. No. 10/927,759, filed Aug. 27, 2004.

II. BODY PORTIONS

The bone prostheses may include a body portion configured to secure a head of the prostheses to bone. The body portion may include a stem to be placed into and secured to a bone, and, if formed by a modular body component, a coupling region to engage a discrete head component. In some examples, the body portion may include a stop or shoulder that restricts entry of the stem into bone and/or a spacer region that spaces the head of the prosthesis from the stem and/or bone.

The stem may have any suitable shape, size, and/or structure that permits the stem to be received in a bone and secured to the bone. The stem may be elongate, for example, having a length based on (1) the length of the bone, (2) the structure of the medullary canal into which the stem is to be placed, and/or (3) the load to be placed on the prosthesis, among others. The stem may be configured to extend any suitable length into a bone, including less than about one-tenth, one-eighth, one-fourth, one-half, or three-fourths the bone's length, or substantially the entire length of the bone. The stem may be linear or nonlinear, that is, bent to follow a curved/arcuate or angular path. The path the stem follows may lie in one plane or may be three-dimensional. The stem may have a diameter that permits the stem to be received in a bore in the bone and restricts lateral movement therein. Accordingly, the width/diameter of the stem may be approximately equal to the diameter of the bore, for example, slightly oversized so that the stem can be press-fit into the bore and/or received snugly therein, or slightly undersized so that the stem can be received easily in the bore. Alternatively, the stem may be substantially undersized to permit adjustable positioning, such as side-to-side positioning and/or tilting before the stem is secured to bone. The stem may have a generally constant width/diameter or may taper toward the distal end of the stem. The taper may occur along more than half of the stem or may be restricted to a distal one-half, such as a distal tip region of the stem. The stem may have a cross-sectional shape that is circular to allow rotation (twisting motion) in the bore during and/or after installation, or may be noncircular (e.g., elliptical, oval, ovoid, rectangular, polygonal, and/or may be shaped according to the cross-sectional shape of a target medullary canal, among others) to restrict rotation in the bore. In some examples, the stem may include ridges and/or grooves extending axially, circumferentially, and/or helically (such as a thread), or may lack such ridges and/or grooves. In some examples, the stem (and/or any other suitable regions of the prosthesis, such as a head component) may include indicia such as references marks and/or symbols (such as letters/words, numbers, and/or the like). The indicia may identify the stem (or head component) (such as according to size (e.g., length and/or diameter), target bone, target side (left/right), etc.) and/or may mark axial and/or angular positions on the stem (or a head-stem spacing), among others. Accordingly, the indicia (such as reference marks) may be arrayed axially and/or circumferentially. The stem may have one or more openings, for example, to receive rigid or flexible fasteners or guides, such as bone screws, wires, pins, and/or sutures, among others. The stem may be rigid or flexible.

The coupling region, also termed a mating structure, may have any suitable position and/or structure that permits engagement with a head component of the prosthesis. The coupling region may be configured to be disposed at least substantially external to the bore of the bone into which the stem is placed or may be disposed at least partially or completely internal to this bore. The coupling region may include one or more projections and/or openings/depressions to be received by, or to receive, complementary structure of the head component. The coupling region may have a fixed and/or adjustable disposition in relation to the stem. Further aspects of coupling mechanisms that may used to couple body and head components are included below in Sections IV and VII.

The body portion may include a stop or shoulder that restricts entry of the body portion into the bore of the bone. The stop may be disposed on an exposed or external region of the body portion, or may be disposed on an internal region of the body portion. In some examples, the stop may be defined by a projection(s) and/or a widened region of the body portion (a region wider than the stem). For example, the stop may be a flange, a collar, one or more knobs, etc. In some examples, the stop may be configured to be movable in relation to the stem, such as by rotational and/or axial motion. For example, the stop may be a threaded collar received by a threaded portion of the stem or by a piece of the body component.

The spacer region may space the coupling mechanism from the stem. Accordingly, the spacer region may be disposed external to the bore of the bone and may include the stop or shoulder. The spacer region may be configured to have any suitable length (a characteristic dimension measured parallel to the long axis of the stem). In some embodiments, a set of body portions may be fabricated with a range of different lengths of spacer regions differing by any suitable distance, such as increments of one, two, and/or four mm, among others. In exemplary embodiments, the lengths may be about 0-20 mm, for example, about 0, 2, 4, and 8 mm (see Example 2), among others. Therefore, the head of a prosthesis may be positioned according to which spacer region is selected. In some embodiments, the spacer region may be adjustable, for example, by moving the stop and/or the coupling region in relation to the stem, among others.

The body portions may be formed integrally with their corresponding head portions or may be formed as separate body components to be assembled with head components. Each body component may be a single piece or an assembly of two or more pieces. In some examples, the body component may include a stem piece for insertion into bone, and a coupling piece formed separately. The coupling piece may include a coupling region and a spacer region. Accordingly, coupling pieces may be modules fabricated with different lengths to permit selection of a suitable spacing of the prosthetic head from the stem piece. In some examples, the body component may include at least two pieces: an outer piece and an inner piece. The outer piece may define an axial bore in which the inner piece (and/or a head component) can move axially and/or rotationally. Axial motion of the inner piece may be restricted, for example, by a collar or other stop structure, either uni-directionally or bi-directionally, among others.

III. HEAD PORTIONS

The bone prostheses may include a head portion configured to articulate with an opposing skeletal member. The head portion may include a head having one or more articulation surfaces, and a coupling region or mating structure to engage a body component, among others.

The head portion may have any suitable shape, size, and disposition relative to the stem. In some examples, the head portion may include a prosthetic head corresponding generally in shape and size to an anatomical head of a bone, or a portion thereof. The prosthetic head may be circular, elliptical, oval, ovoid, and/or asymmetrical bilaterally, among others. The prosthetic head may include a smooth articulation surface.

The prosthetic head may have any suitable disposition relative to the stem of a prosthesis. For example, the prosthetic head may be centered over, or laterally offset from, the stem of a prosthesis. Furthermore, the prosthetic head (and particularly a proximal surface thereof) may be configured to be in angular alignment with the stem (that is, square with), or angularly offset from the stem (that is, tilted). Accordingly, the prosthetic head may have any suitable angular offset defining any suitable angle relative to the stem. For example, the angle may be about 0-20, 2-15, or about 3-10 degrees, among others. A tilted head may provide superior performance over a nontilted head. For example, a tilted prosthetic head for the radius may provide better contact with the capitellum and thus better stability than a nontilted head, throughout the range of motion of the arm. In some examples, the prostheses may include a set of head components having two or more different fixed angular offsets or tilts (including or excluding no tilt). The angular offset may be configured to be about any suitable axis defined by installation in a target bone, including about a substantial medial-lateral axis and/or about a substantial anterior-posterior axis of a prosthesis recipient. In some examples, the angular offset may be adjustable within a prosthesis, for example, by rotating the head component relative to the body component. Thus, the angular offset may be adjustable continuously or to a set of predefined, discrete offsets. The prosthetic head (and/or head portion) may have any suitable length (measured parallel to the axis of the stem) and the length may be generally constant or may vary circumferentially and/or radially.

The coupling region of a head component may have any suitable structure and disposition that permits the head component to be assembled with a body component. This coupling region may be formed integrally with the prosthetic head of a head component or may be a separate piece(s). Accordingly, this coupling region may have a fixed and/or adjustable relation to the prosthetic head of a prosthesis. This coupling region may be included in prosthetic heads of the prostheses, such as an opening formed therein, or may be distinct from the prosthetic heads, such as a projection extending therefrom, or an opening or projection defined by, or extending from, a narrowed neck region disposed adjacent (stemward) the prosthetic head. In some examples, head components may be formed with coupling regions having a different spacing from the prosthetic heads of the head components (and/or an articulation and/or proximal surface thereof), so that the height of the prosthetic head can be selected according to which spacing is selected. In some examples, the prostheses may include a set of head components having prosthetic heads of different lengths (measured axially). In some examples, the prostheses may include a set of head components having prosthetic heads of substantially the same length, and narrowed/tapered neck regions of different lengths. Maintaining a generally constant length/size of the prosthetic head, while varying the length of the neck region (or of a prosthetic neck formed by the head and/or body components) may be advantageous because this strategy can more accurately re-create the structure of missing bone.

The head portions may be formed integrally with their corresponding body portions or may be formed as separate head components to be assembled with body components. Each head component may be a single piece or an assembly of two or more pieces.

IV. COUPLING MECHANISMS

Body and head components of the prostheses may be assembled using any suitable coupling mechanism. A coupling mechanism, as used herein, is any mechanism that connects the body and head components to one another.

The coupling mechanism may assemble the body and head components by any suitable relative motion of these components. The relative motion may be translational motion and/or rotational motion. In some examples, the relative motion for coupling may be restricted at least substantially to a plane disposed generally transverse to a long axis defined by the body component. The translational motion may be transverse motion directed generally transverse to the long axis defined by the stem of the prosthesis and/or axial motion generally parallel to this long axis. The rotational motion may be about the long axis defined by the stem and/or about any other suitable axis. In some embodiments, the coupling mechanism may permit assembly of the body and head components without substantial axial movement of these components.

The coupling mechanism may include generally complementary mating structures formed on the head and body components. These mating structures may include, for example, at least one projection configured to be received by at least one opening or cavity. The projection(s) and the opening(s) may be formed on either component. The mating structures may be configured to selectively permit and/or restrict translational and/or rotational motion. In some examples, the coupling mechanism may permit rotational motion after the head and body components have been assembled, for example, forming a movable joint that permits the head component to have an adjustable pitch and/or roll. In some examples, a head component that is movable after assembly may be fixed in position using a detent mechanism (see below). The coupling mechanism also may permit or restrict transverse motion. The transverse motion may be unrestricted in opposing directions or may be restricted selectively in one of two opposing directions by a wall and/or tapered mating structures, among others. Exemplary mating structures may include complementary dovetail structures (tapered or nontapered), a T-shaped projection received in a T-shaped recess, a tapered axial projection received in a tapered axial recess (a Morris taper), and/or the like. Further examples of coupling mechanisms are described below in Section VII.

The prostheses may include a detent mechanism to restrict uncoupling of the body and head components after their assembly using the coupling mechanism.

The detent mechanism may be actuated at any suitable time by any suitable action. The detent mechanism may be actuated during assembly of the body and head components. For example, the detent mechanism may be actuated by transverse motion of the head component during assembly. Alternatively, or in addition, the detent mechanism may be actuated by a distinct motion of the head or body component after assembly, such as rotation of the head component about the long axis of the stem, a different transverse motion of the head component than that used for initial coupling, etc. In some examples, the detent mechanism may be actuated by moving a distinct catch, stop, button, lever, retainer, fastener (such as a screw, bolt, nut, pin, etc.), and/or the like, that is formed in the body and/or head component or is assembled as a separate component with the body and/or head components.

V. KITS

The prostheses may be provided in kits. The kits may include and/or provide prostheses, body components, and/or head components of different sizes/shapes. The kits also may provide fasteners, positioning jigs, measuring devices, drills, reamers, instructions for use, etc. Some or all of the kit components may be provided in a sterile condition.

The kits may include and/or provide any suitable prostheses. The prostheses may be unitary or modular in construction and may have a plurality of different head-stem spacings. The prostheses also may include, for each head stem-spacing, two or more prostheses with a different head diameter, a different stem diameter, a different head tilt (including lack of tilt), and/or a different side of use (left or right) in a recipient. In some examples, the kits may include at least one head component and a plurality of body components, which may be assembled in pairwise head-body combinations to provide the set of prostheses. In some examples, the kits may include at least one body component and a plurality of head components, which may be assembled in pairwise head-body combinations to provide the set of prostheses.

In some examples, the kits may include one or more positioning jigs. These jigs may be configured to be connected to prostheses, such as through body and/or head portions/components of the prostheses. The jigs also may be configured to adjust the height (axial disposition) and/or angular disposition of the prostheses relative to bone, through, for example, reference marks, axial/angular adjustment mechanisms, and/or alignment structures, among others, disposed on the jigs. In some examples, the jigs may include guide structures configured to direct hole-forming devices, such as drills, and/or to direct placement of fasteners into openings of the prostheses.

The kits also may include fasteners to secure the head and body components to one another and/or to bones, and/or one or more measuring devices and/or trial prostheses. Further aspects of kits, trial prostheses, measuring devices, jigs, and modular prosthetic components are described below in Section VII and in the following patent and patent application, which are incorporated herein by reference: U.S. Pat. No. 6,494,913, issued Dec. 17, 2002; and U.S. patent application Ser. No. 10/927,759, filed Aug. 27, 2004.

VI. METHODS OF INSTALLING BONE PROSTHESES

Bone prostheses may be installed in a bone (or bones) by any suitable methods. Exemplary operations that may be included in a method of installation and/or prosthesis selection are included below. The operations may be performed in any suitable combination, in any suitable order, and any suitable number of times.

A bone may be selected for replacement of an end (a head) of the bone. The bone may be any suitable bone, such as a left or right radius bone for replacement of a proximal head of the radius bone.

The bone may be prepared for receiving a prosthesis. Such preparation may include any suitable surgical procedures for monitoring a patient's vital signs, preparing a sterile field, debriding and disinfecting an injury, etc. Such preparation also may include forming an externally accessible bore in the bone, for example, by drilling a hole in the end of the bone, broaching and/or reaming the medullary canal of the bone to widen and/or define the diameter of the canal, cutting off the end of the bone, and/or the like. The preparation may remove the head of the bone and a suitable length of the neck of the bone adjacent the head, to create a missing region of the bone. Alternatively, or in addition, removal may be performed partially or completely by an injury to the bone.

The site of installation may be measured to determine a size of prosthesis that would be suitable. This measurement may include measuring a width and/or length of the bore, a width and/or length of a remaining portion and/or end surface of the bone, a spacing of the remaining end surface of the bone from one or more adjacent skeletal members, and/or the like. In some examples, measurement may be performed with a measuring device, such as a height gauge. Accordingly, the measuring device may be a trial prosthesis that generally replicates the disposition of a more permanent ("implant") prosthesis. The measuring device may include a measurement mechanism that indicates one or more measured dimension(s) and/or a suitable size (or identity) of an implant prosthesis (or implant component), among others. A portion of the measuring device may be positionable to contact the adjacent skeletal member(s), to achieve proper measurement. Alternatively, or in addition, measurement may be performed with another measurement device (such as a ruler, a tape measure, a spacer element, calipers, etc.) or may be determined from a template visible by x-ray, fluoroscopy, etc. Further aspects of measuring devices and trial prostheses are included below in Example 6.

A prosthesis may be selected. Selection may include selecting a prosthesis having integral head and body portions or having modular head and body components. In some examples, the selection may be performed based on one or more measurements performed with a trial prosthesis and/or a measurement tool(s) such as a spacer element. In some examples, a body (and/or head) component may be selected from a set of body (and/or head) components having different spacer regions. In some examples, a head (and/or body) component may be selected from a set of head (and/or body) components that couple to the body (and/or head) component at different angular dispositions.

The stem may be placed in the bore of the bone. In some examples, the stem may be press-fit into the bore, for example, by hammering a body component into the bone. Alternatively, or in addition, the stem may be cemented to the bone with an adhesive and/or may be secured with fasteners (such as bone screws, etc.), among others. In some examples, the fasteners may be placed through openings in the stem using a guide connected to the prosthesis. The depth of insertion of the stem may be determined by any suitable mechanism, including a stop structure on the prosthesis that restricts further entry, reference markings on the stem, a positioning jig, and/or by a wall of the bore formed in the bone, among others. In some examples, the depth of insertion of the stem and/or the spacing of the coupling region of the body component from the stem may be adjusted.

A head component and a body component may be assembled (before and/or after placement of the stem into bone). The head and body components may be assembled by generally transverse (e.g., lateral to medial motion of the head component onto the body component) and/or axial motion of a head component towards the body component. This motion may be in a plane and/or along an axis, and may mate complementary mating structures. In addition, this motion may lock the head component to the body component, to restrict its uncoupling from the body component and/or to fix the position of the head component. Alternatively, the head component may be locked by actuation of any suitable detent mechanism, including rotating the head component, and/or placing a retainer into engagement with the head and/or body components, among others. Further aspects of detent mechanisms and actuation of detent mechanisms are described below in Section VII.

The position of the head component (and/or body component) may be determined and/or adjusted. Determining the orientation of the head component may be based, for example, on an asymmetrical profile of the head component. The asymmetrical profile may be determined by direct visual inspection and/or using instrumentation, such as a fluoroscope. Alternatively, or in addition, the position of the head component (and/or prosthesis) may be adjusted based on a reference mark on the head component (and/or prosthesis). In some examples, the position of the reference mark may be checked and/or adjusted while viewed through a lateral incision in an arm.

VII. EXAMPLES

The following examples describe selected aspects and embodiments of the present teachings, including prostheses for replacing ends of bones, trial prostheses to facilitate selecting implant prostheses and components thereof from a kit, and exemplary methods of selecting and/or using the prostheses. These examples are included for illustration and are not intended to limit or define the entire scope of the present teachings.

Example 1

Radial Head Prosthesis with Axial Assembly

This example describes an exemplary radial head prosthesis with head and body components that mate axially; see FIGS. 4-10. Further aspects of this exemplary prosthesis are described above in relation to FIGS. 1-3.

FIGS. 4-8 show various views of head component 72 of prosthesis 42.

FIG. 4 shows a top view of the head component. The head component may be elliptical when viewed from the proximal surface of the head. Accordingly, the width of the head between medial and lateral surfaces 62, 64 may be greater than the width of the head between anterior surface 92 and posterior surface 94. The head component may include a proximal surface 96 that includes a concave articulation surface 52 and a rim 98 extending around the articulation surface. Articulation surface 52 may be offset somewhat towards lateral surface 64 from the center of the head component (see FIG. 5 also). Exemplary offsets include about 0.5 to 3 mm, or about one mm, among others. Articulation surface 52 may correspond to a portion of a sphere having a radius that substantially matches the radius (dimension) of a capitellum with which this surface articulates. In particular, the proximal articulation surface may slide along the capitellum surface during flexion-extension of the elbow joint and may pivot on the capitellum surface during pronation-supination movement of the forearm.

Figure 5:
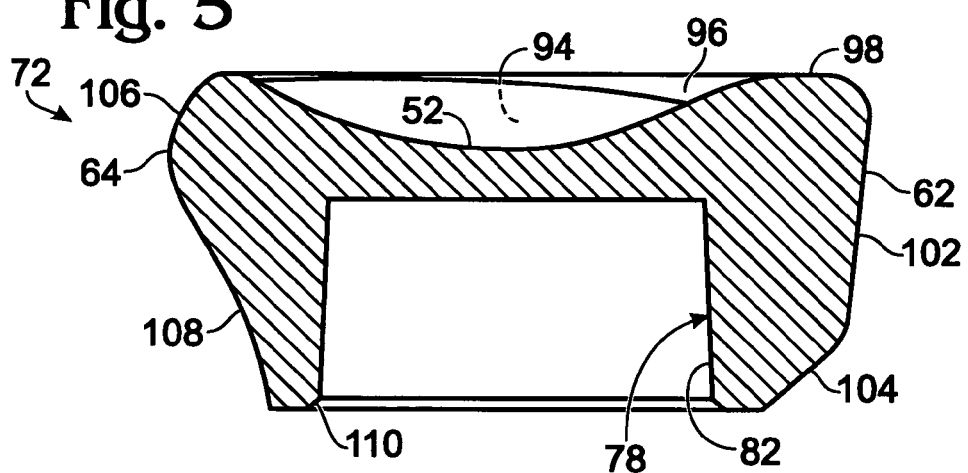
FIG. 5 is a sectional view of the head component of FIG. 4, taken generally along line 5-5 of FIG. 4.

FIG. 5 shows a medial-lateral sectional view of head component 72, as viewed towards posterior surface 94 of the head component. The exterior side wall of the head component may define both the head of the prosthesis, and, optionally, a part or all of the neck of the prosthesis. Furthermore, the side wall may have distinct, asymmetrical profiles on the medial and lateral sides of the head component. In particular, a proximal region 102 of a medial surface 62 of the side wall may be configured for articulation with the ulna and may have a substantially linear and/or convex profile. The linear profile (formed at least substantially of one or more one line segments) may be disposed parallel to the long axis of the prosthesis or may slant somewhat, as shown here, such as about 2-10 degrees, or about 5 degrees, among others. Accordingly, the medial surface may taper toward the body of the prosthesis. A distal region 104 of the medial surface may slant inward from the proximal region of this surface to form a portion of the neck. This distal region may be linear, as shown here, or concave or convex.

The linear profile, or a variation thereof, may have any suitable size and disposition on the head component. For example, a linear region of the linear profile may be formed on any suitable extent of the head component, such as at least about one-half, three-fourths, or all of the circumference of the head component, among others. The width of the linear profile (measured generally parallel to the long axis of the prosthesis) may be constant (or increase), or the length may decrease away from the circumferential midpoint of the medial surface, so that the side articulation surface of the head tapers circumferentially and/or transitions gradually to an increasingly arcuate profile as the side wall of the head extends circumferentially toward the lateral surface (see FIGS. 6 and 13). Furthermore, the angular disposition of this linear profile (the angle formed with the long axis), at positions around the head, may be constant or may vary (see FIGS. 6 and 13).

The lateral surface may have a more arcuate or curved profile than the medial surface (see FIG. 5). For example, a proximal region of the lateral surface, shown at 106, may be convex to form part of the head, and a distal region of the lateral surface, shown at 108, may have a linear or concave taper to form part of a prosthetic neck.

The head component may include mating structure 78. The mating structure may include, for example, a frustoconical cavity 82 with a beveled perimeter 110 to guide mating. In some embodiments, the cavity may have a noncircular cross-section (elliptical, polygonal, etc.), to restrict twisting movement of the head component on the body component.

Figure 6:
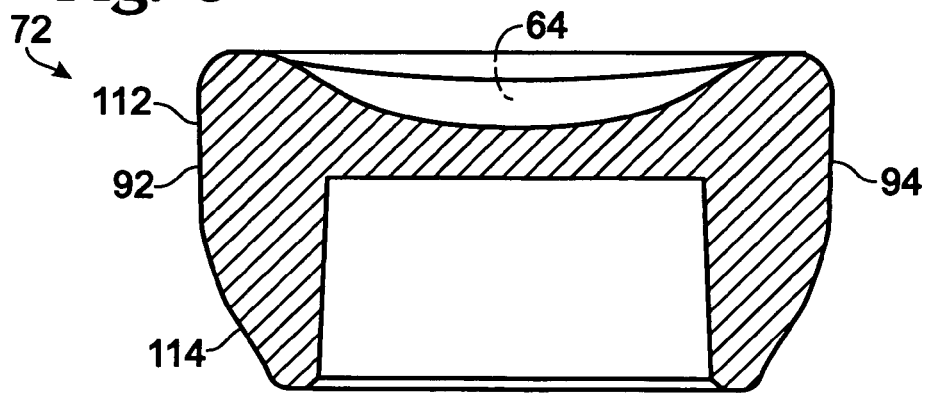
FIG. 6 is a sectional view of the head component of FIG. 4, taken generally along line 6-6 of FIG. 4.

FIG. 6 shows an anterior-posterior sectional view of head component 72, as viewed towards lateral surface 64 of the head component. Anterior and posterior surfaces 92, 94 may have mirror symmetry at this mid-plane of the head component (or may be asymmetrical (see FIGS. 12 and 13)). Furthermore, the anterior and posterior surfaces may have profiles that are identical or distinct from the profile of the medial surface. For example, the anterior and posterior surfaces may have a smaller proximal region 112 (than the medial surface) with a linear profile for articulation, and a larger distal region 114 (than the medial surface) for forming the neck. Accordingly, the anterior and posterior surface may provide a smooth, gradual transition between the medial and lateral profiles of the head component.

FIGS. 7 and 8 show a lateral view and a bottom view, respectively, of the head component. The side wall of the head component (and/or the proximal surface), and particularly, lateral surface 64 may include a reference mark 116 to facilitate orienting the head of the prosthesis during installation. In some examples, the reference mark may indicate a lateral surface of the head (for orientation laterally in a recipient relative to a lateral incision), with the forearm in a neutral position (midway between full supination and full pronation). The reference mark also may indicate a position of the head (and head component) directly opposite the circumferential midpoint of the side articulation surface of the head. A surgeon may place the reference mark facing approximately lateral during installation of the prosthesis. In some examples, the reference mark may be placed offset somewhat from directly lateral, such as 0-40 degrees anterior to directly lateral, to accommodate a posterior offset of the radial notch from directly medial.

FIGS. 9 and 10 show a side view and a bottom view, respectively, of body component 74 of the prosthesis. The body component may include an internal portion or stem 50 for placement into bone and an external portion 118 to be disposed outside of bone.

Stem 50 may (or may not) have a generally circular cross section to permit (or restrict) rotation of the stem during and/or after initial placement in bone (e.g., to facilitate orienting reference mark 116 after assembly with the head component (see FIGS. 7 and 8)). For example, the stem may have a cylindrical section 120 and/or a tapered section 122. The cylindrical section may be disposed more proximally than the tapered section. The end of the stem may be rounded, shown at 124, or pointed, as appropriate. In some examples, the stem may include one or more grooves, such as axial flutes 126. The grooves may, for example, facilitate securing the stem to bone, such as by permitting bone ingrowth into the grooves and/or by holding bone cement, among others.

External portion 118 may include spacer region or collar 88 and/or mating post 80. The collar may extend vertically or may have a linear, concave, and/or convex profile. In some examples, the collar may taper stemward over a portion or all of its length (measured parallel to the long axis of the stem). The collar (or other stop structure) may define a shoulder 68 that extends laterally (outward) from the stem, to engage the end surface of the bone and thus position the stem in bone. In some examples, the shoulder may define a planar surface 128 (see FIG. 10) that is substantially perpendicular to the long axis of the stem.

The body component also may include one or more openings. For example, the body component may include a threaded opening 129 disposed in the external portion (e.g., in the mating structure). The threaded opening may be accessible from the proximal end of the body component, and may be coaxial with the stem. Accordingly, the threaded opening may be disposed in the mounting structure, and, optionally, may extend into the collar and/or stem. The threaded opening may be used, for example, for receiving a threaded tool (such as a fastener or threaded rod, among others) that can be threaded into the opening for engagement and manipulation of the body component (for example, insertion, axial positioning, removal, re-orientation (twisting) about the long axis, etc.)

Example 2

Exemplary Set of Body Components

This example describes an exemplary set of body components for mounting a head component at different distances from a stem and/or an end surface of bone; see FIG. 11.

A system 130 for bone replacement may include a set 132 of two or more body components 134, 136, 138, 140. The body components may be configured to mount a head component 72 (and particularly a proximal surface of the head component) at different distances from the stem and/or shoulder of the body components (at different heights). Accordingly, the body components may have spacer regions or collars 142, 144, 146 of different lengths (measured axially), which may partially or completely circumscribe the stem. Thus, a single head component, such as head component 72 (shown in phantom outline), mated with each of the body components positions the head component at different distances from the stem and the (cut or broken) end of bone, to accommodate different lengths of missing bone and/or different joint structures, and/or to restore the original overall length of the radius.

Body component 134 has no collar to provide a shoulder. Accordingly, in this embodiment, the head component may provide a shoulder that engages the end of the bone.

Example 3

Radial Head Prostheses with a Tilted Head

Figure 12:
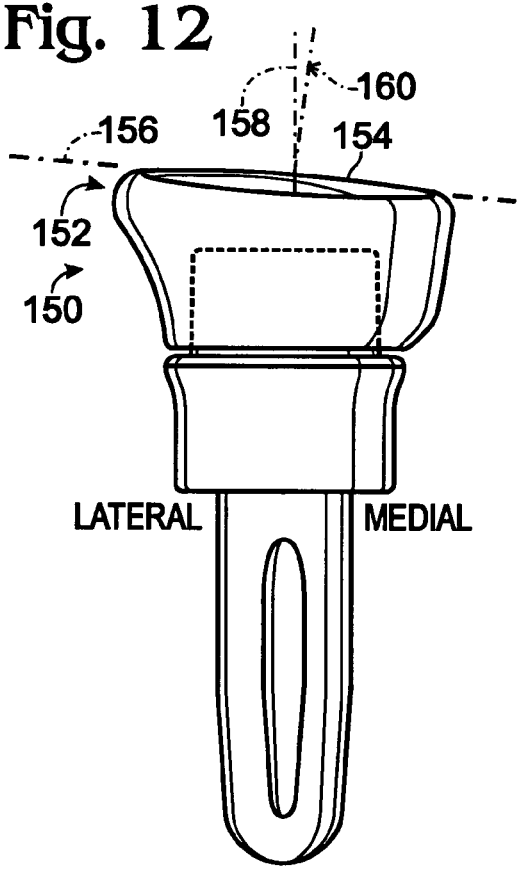
FIG. 12 is a posterior side elevation view of an exemplary radial head prosthesis with a tilted head, in accordance with aspects of the present teachings.
Figure 13:
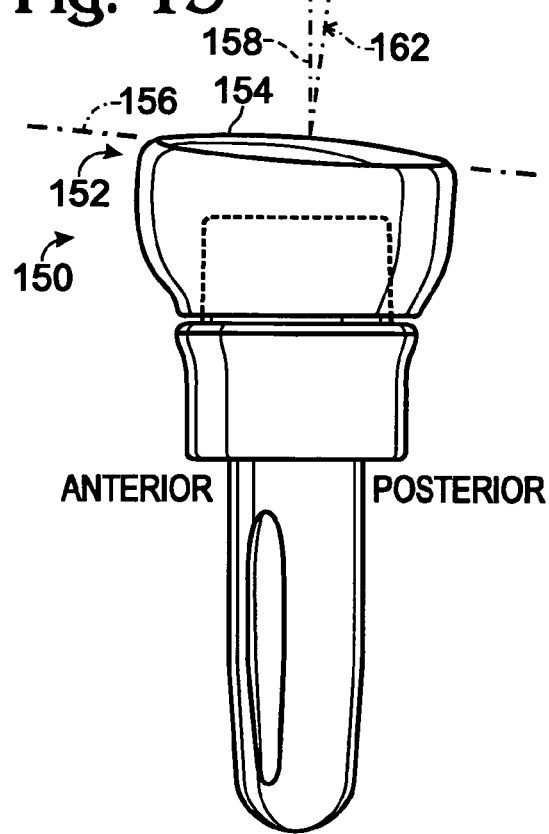
FIG. 13 is a medial side elevation view of the radial head prosthesis of FIG. 12.
Figure 14:
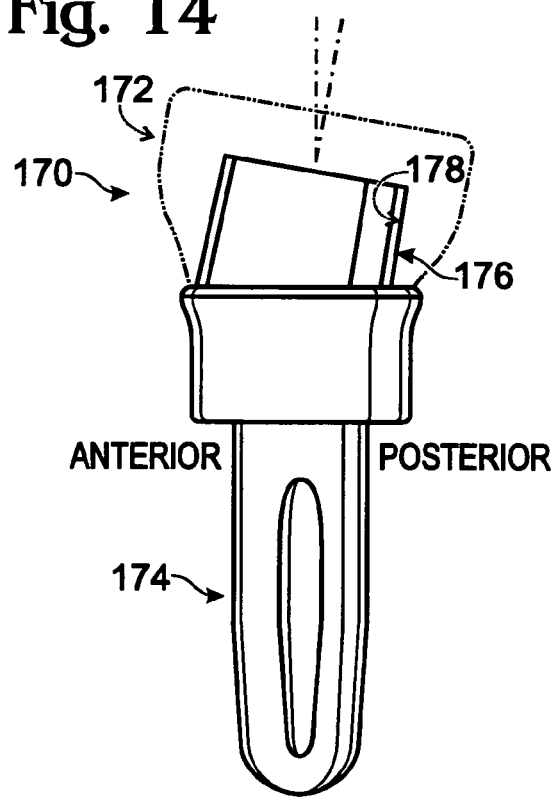
FIG. 14 is a medial side elevation view of another exemplary radial head prosthesis with a tilted head, in accordance with aspects of the present teachings.

This example describes exemplary radial head prostheses with heads having a fixed, tilted disposition; see FIGS. 12-14.

FIGS. 12 and 13 show views of an exemplary radial head prosthesis 150 with a tilted head 152. In particular, proximal surface 154 defines a tangential plane 156 that is tilted from orthogonal to long axis 158 of the prosthesis. The angular tilt, shown at 160 and 162 in FIGS. 12 and 13, may be, for example, about 2-15 degrees or about 5-10 degrees, about one or more axes.

In the present illustration, anatomical dispositions ("lateral," "medial," "anterior," and "posterior") are indicated approximately for a properly installed prosthesis with the forearm in a neutral position (about midway between fully supinated and fully pronated). These anatomical directions may be approximate directions because the prosthesis may be installed with an angular offset (a twist about the long axis) from perfect alignment with these axes, for example, about 20 degrees. This angular offset may correspond to the posterior angular offset of the radial notch from directly medial.

FIG. 12 shows the proximal surface of the head may be tilted in a medial direction (about a substantially anterior-posterior axis of a person (more generally, a recipient)). In addition, FIG. 13 shows the proximal surface of the head also or alternatively may be tilted in a posterior direction (about a substantially medial-lateral axis of the person). For a tilt that eliminates bilateral symmetry, such as the tilt shown in FIG. 13, a head component and/or prosthesis may be configured for use on either the right side or the left side of a recipient, but not both. Prosthesis 150 lacks mirror image symmetry because of the posterior tilt of the head and thus is configured only to replace a left radial head. A mirror image version of prosthesis 150 may be fabricated and selected to replace a right radial head. In some embodiments, a prosthesis with a tilted head may be unitary rather than provided by modular components, as shown here.

The mating structure of the head and/or body components may be aligned with the distal end of the head component (closest to the stem) or may be tilted relative to this distal end. For example, FIG. 14 shows a radial head prosthesis 170 in which the head component 172 and body component 174 have tilted mating structures 176, 178.

Example 4

Radial Head Prostheses with Dovetail Mating Structures

Figure 15:
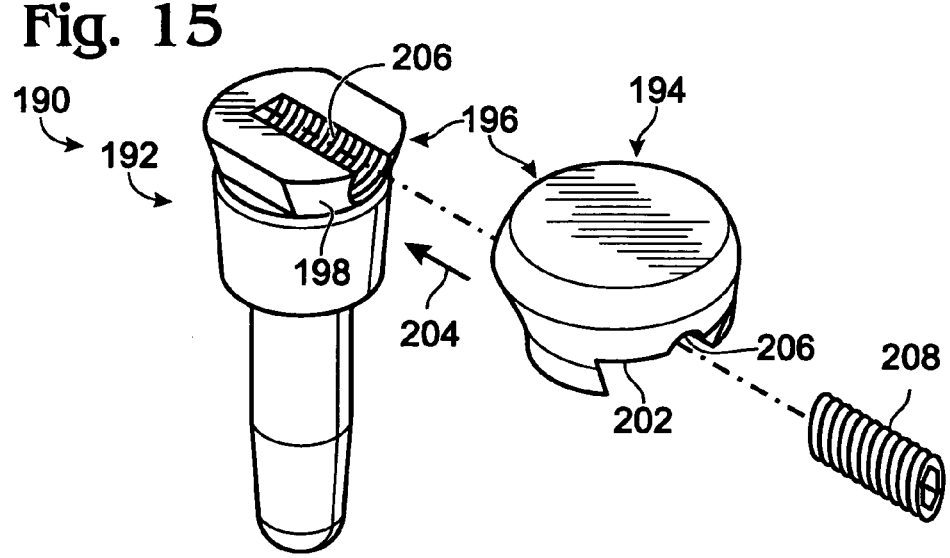
FIG. 15 is an exploded view of an exemplary radial head prosthesis with a head component that mounts transversely, in accordance with aspects of the present teachings.
Figure 16:
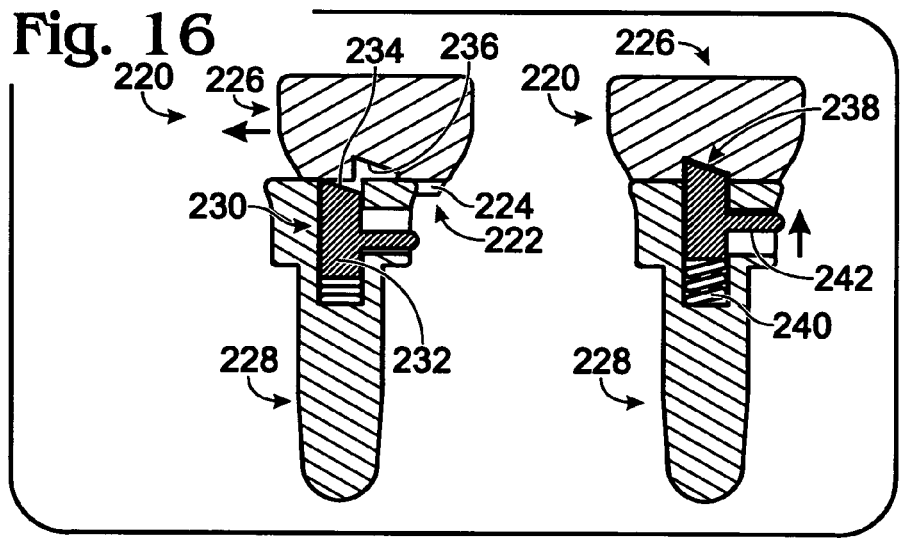
FIG. 16 is a sectional view of another exemplary radial head prosthesis with a head component that mounts transversely, in accordance with aspects of the present teachings.

This example describes exemplary radial head prostheses with a head component that mates with a body component by transverse motion; see FIGS. 15 and 16.

FIG. 15 shows a prosthesis 190 including a body component 192 and a head component 194. The head component here and in the prostheses described below may have any of the features of head components described elsewhere in the present teachings. The head and body components may be assembled using a dovetail coupling mechanism 196. In particular, the body component may have a dovetail-shaped platform 198 and the head component may have a complementary dovetail-shaped cavity 202. However, in other examples these dispositions may be reversed. In any case, the head component thus may be mounted on the body component by transverse motion of the head component, for example, in a lateral to medial direction, shown at 204, with the body component installed in bone. One or both dovetail-shaped structures may be tapered, so that the head component can be seated onto the body component by motion in one direction (opposing the taper), and removed by motion in the opposing direction (in the direction of the taper).

The prosthesis may include a detent mechanism with a retainer to restrict removal of the head component. For example, the detent mechanism may include a threaded (or nonthreaded) opening 206 formed cooperatively by platform 198 and cavity 202 when the head component is mounted on the body component. Opening 206 may be accessible from the lateral side of the body component, so that a retainer, such as a screw 208, can be placed into this opening peri-operatively. In some examples, the retainer may be a pin that is press-fit or snapped into position. Alternatively, the retainer may be a cap that prevents removal of the head component. The cap may be configured to be secured in the cavity, such as by a snap-fit, with an adhesive, and/or with one or more fasteners, to block transverse motion of the head component on the body component.

FIG. 16 shows another example of a radial head prosthesis 220 with a dovetail coupling mechanism 222 (only a portion of a dovetail-shaped cavity 224 of the head is shown in this view). The prosthesis has a head component 226 in a partially mounted (left side of figure) and fully mounted (right side of figure) configuration on a body component 228. The body component may include a biased detent mechanism 230 that restricts removal of the body component. In particular, the detent mechanism may include a spring-biased retainer or catch 232. The retainer may be retracted into the body component by contact of a beveled surface 234 of the retainer against the head component (or by operation of a lever (see below)). When the head component is advanced fully onto the body component, retainer 232 may spring upward into an aligned recess 236 of the head component, shown at 238, and held in this position by a biasing element (such as spring 240), to restrict removal of the head component. A lever 242 may be connected to the retainer to allow the retainer to be selectively retracted, so that the head component can slide transversely off the body component, if desired. In some examples, the dovetail platform and/or the catch and the release may be placed on the head component, and/or the recess in the body component.

Example 5

Radial Head Prostheses with Rotation-Based Coupling Mechanisms

This example describes exemplary radial head prostheses that include a rotation-based coupling mechanism; see FIGS. 17-23.

Figure 17:
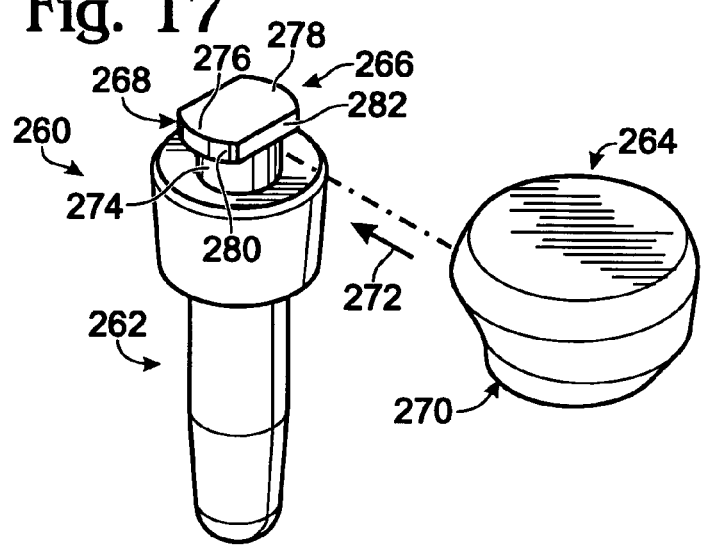
FIG. 17 is an exploded view of an exemplary radial head prosthesis with a head component that mounts by transverse and rotational motion, in accordance with aspects of the present teachings.
Figure 18:
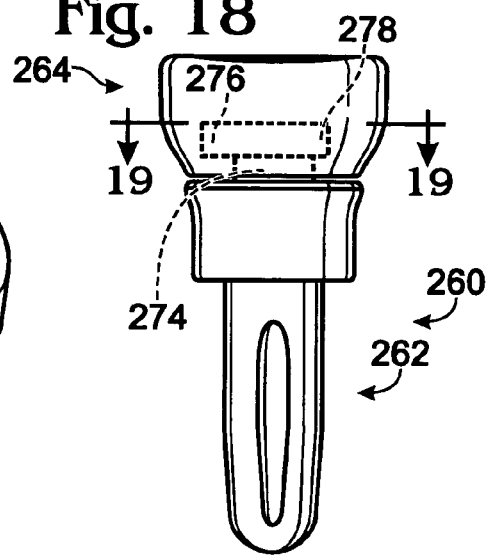
FIG. 18 is a side elevation view of the radial head prosthesis of FIG. 17 in an assembled configuration.

FIGS. 17 and 18 show an exploded view and an assembled view, respectively, of an exemplary radial head prosthesis 260. The prosthesis may include a body component 262 and a head component 264 that mounts on the body component using coupling mechanism 266. The coupling mechanism may include an offset T-shaped mounting projection 268 formed on the body component and a generally complementary offset T-shaped cavity 270 formed in the head component. Alternatively, the projection may be on the head component and the cavity in the body component. Head component 264 may be placed on body component 262 by transverse motion, shown at 272, so that projection 268 is received in cavity 270, and then advanced to a seated configuration by rotation.

Mounting projection 268 may include a base or support 274 and flanges 276, 278 formed asymmetrically (noncentered) on the support. The flanges may form a flange structure having opposing arcuate sides 280 and opposing planar sides 282.

FIG. 19 shows a sectional view of radial head prosthesis 260 prior to assembly. Cavity 270 may include an offset channel 284 that receives the offset flanges. Accordingly, the head component may be placed onto the body component by motion in transverse direction 286.

FIG. 20 shows the head component partially advanced onto the body component by transverse motion.

FIG. 21 shows the head component fully advanced translationally onto the body component. The head component then may be rotated in a direction shown at 288.

FIG. 22 shows the prosthesis after rotation of the head component by about one-half revolution, until longer flange 276 engages a narrowed region of the cavity, shown at 290, so that engagement of the cavity wall with the flange blocks further rotation in the same direction. Rotation of about one-half turn may place the mouth of the cavity of the head component on the lateral side of the radius, so that the mouth is accessible to the surgeon (to implement a detent or lock mechanism, such as by placement of a cap, fastener, or other retainer).

FIGS. 22 and 23 show placement of a cap 292 to block reverse rotation of the head. The cap may have any exterior surface that is generally flush with adjacent surface regions of the head component, such as the lateral surface, and may have an interior surface configured to abut the body component, particularly planar side 282. In some examples, the cap may be formed of a resilient material, so that the cap may be snapped into place. Accordingly, the cap may include one or more protrusions 294 (and/or recesses) that mate with complementary recesses 296 (and/or protrusions) of the head component (and/or body component). Alternatively, or in addition, the cap may define an opening for receiving a threaded fastener. In some examples, the threaded fastener may extend through the opening of the cap to be received in a threaded hole of the body and/or head component. For example, base 274 (and/or the flange structure formed on the base) (see FIG. 17) may include a threaded hole that is aligned with an opening in the cap when the head component is fully seated on the body component. In some examples, the cap may be cemented in place with an adhesive. In some examples, the plug may be configured to be removable, for example, by deforming the plug to disengage the projection (s) from the recess(es), by removing the fastener, and/or the like.

Further aspects of prostheses that are assembled by rotation are included in the following provisional patent applications, which are incorporated herein by reference: U.S. Provisional Patent Application Ser. No. 60/552,957, filed Mar. 11, 2004; and U.S. Provisional Patent Application Ser. No. 60/571,008, filed May 13, 2004.

Example 6

Systems with Trial Prostheses

This example describes systems including exemplary trial prostheses and associated instrumentation that may be used to assist selection of (more permanent) implant prostheses and/ or components thereof; see FIGS. 24-29.

FIGS. 24 and 25 show an exploded view and an assembled view, respectively, of a trial prosthesis 310 that may be included in the systems of the present teachings. In particular, the trial prosthesis may be used in conjunction with a set of prostheses, a set of head components, and/or a set of body components, to facilitate selection of a suitable prosthesis and/or prosthetic component for a particular individual and indication. The trial prosthesis thus may serve as a measuring device or height gauge to determine a suitable head size, head height, head angle, and/or stem size, among others. For example, the trial prosthesis may be installed in the proximal radius in place of the natural radial head, then tested for proper function while the arm is moved (e.g., flexed, extended, supinated, pronated, etc.), and then a corresponding implant prosthesis selected.

The trial prosthesis may include a head component 312 and a body component 314. The head and body components may be assembled in an adjustable configuration that permits the head to move axially, shown at 316 (see FIG. 25), relative to the body component. The head component may include a head 318 mounted on a post 320. The body component may include a hollow stem 322 with an axial bore 324 configured to receive the post slidably, so that the head can be moved different distances from the stem. The body component also may include a collar 326 disposed proximally to the stem. The collar may provide a shoulder 328 of increased diameter that engages the end of the radius, to position the stem properly in a bore of the radius. Furthermore, the collar may include a groove 330 configured to facilitate gripping the body component with a holder (and for insertion and/or removal of the trial prosthesis), as described in more detail below.

The trial prosthesis may include a plurality of interchangeable head and/or body components. For example, the trial prosthesis may include a plurality of body components having stems of different diameter (and/or length), to test the fit of different implant body components (of corresponding diameter and/or length) that may be provided by a kit. Alternatively, or in addition, the trial prosthesis may include a plurality of head components (and attached posts) having heads of different diameter, shape, and/or tilt, to allow selection of an implant head component (of corresponding diameter, shape, and/or tilt) from a set of such head components that may be available to a surgeon.

The trial prosthesis may include a detent mechanism 332 (see FIG. 25) that holds the head component at a plurality of predefined positions along axial bore 324. The detent mechanism thus holds the head at a set of predefined distances from the stem. The detent mechanism may include a biased projection 334 disposed on the post and a plurality of depressions 336, such as circular grooves, disposed along the axial bore. When the projection is aligned with one of the depressions, spring 338 pushes the projection outward into the depression, to hold the head at a predefined height above the stem. Application of a sufficient axial force on the head component (and/or body component) may release the head component by forcing the biased projection inward, to allow further axial movement of the head component. Accordingly, the head can be moved to a plurality of predefined heights above (distances from) the stem, to allow testing the function of the prosthesis at each of the head heights. Furthermore, the predefined heights (head-stem spacings) may be designed to correspond to (and substantially match) head heights for different implant prostheses provided by a set, so that a suitable head height identified with the trial prosthesis can be used to select a corresponding implant prosthesis.

Figure 26:
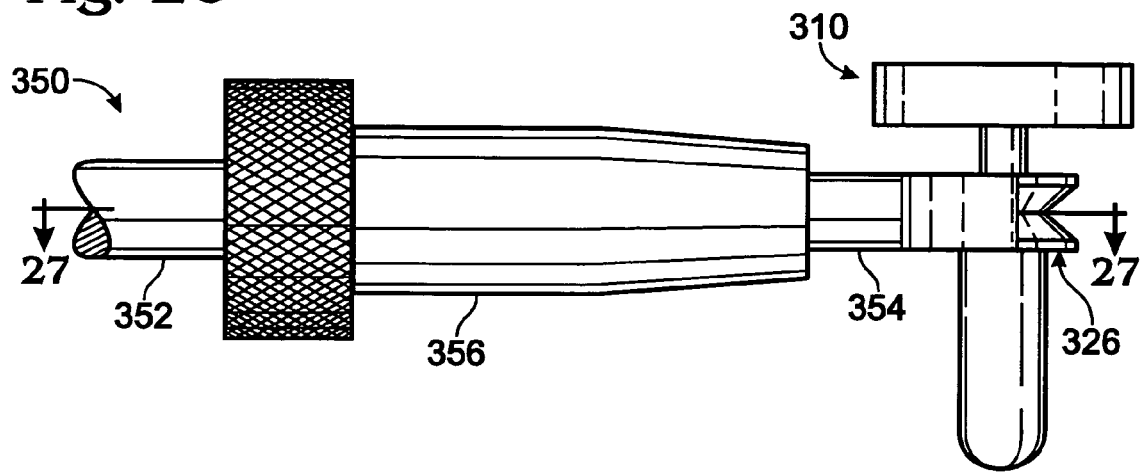
FIG. 26 is a fragmentary side elevation view of an exemplary holder having a locked grip on the trial prosthesis of FIGS. 24 and 25, in accordance with aspects of the present teachings.
Figure 27:
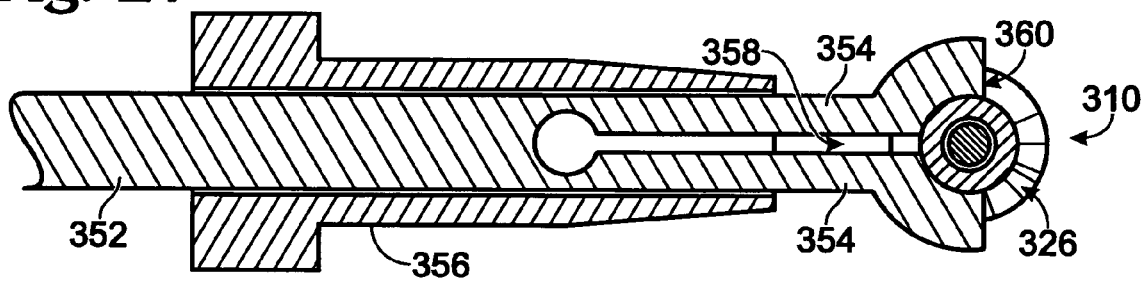
FIG. 27 is a fragmentary sectional view of the holder and trial prosthesis of FIG. 26, taken generally along line 27-27 of FIG. 26.

FIGS. 26 and 27 show a holder 350 gripping the trial prosthesis. The holder may include an elongate handle portion 352, arms 354 that opposingly grip collar 326, and a locking sleeve 356 that slides along the handle portion to lock the holder reversibly onto the collar. The handle portion may have sufficient length to be held by hand. Furthermore, the handle portion may, for example, be knurled or include other suitable structure to facilitate manual manipulation. Arms 354 may be somewhat resilient and separated by a gap 358 that allows the spacing between the arms to change. The arms thus can be spread apart slightly (with the locking sleeve spaced from the arms) when placed onto collar, and than held together (with the locking sleeve over the arms (See FIG. 27)), so that the handle portion can be used to manipulate the trial prosthesis. The arms may extend more than half way around the collar, shown at 360, so that the collar is gripped effectively. The holder, engaged with the trial prosthesis, may be used, for example, to insert, remove, and/or re-position the trial prosthesis.

Figure 28:
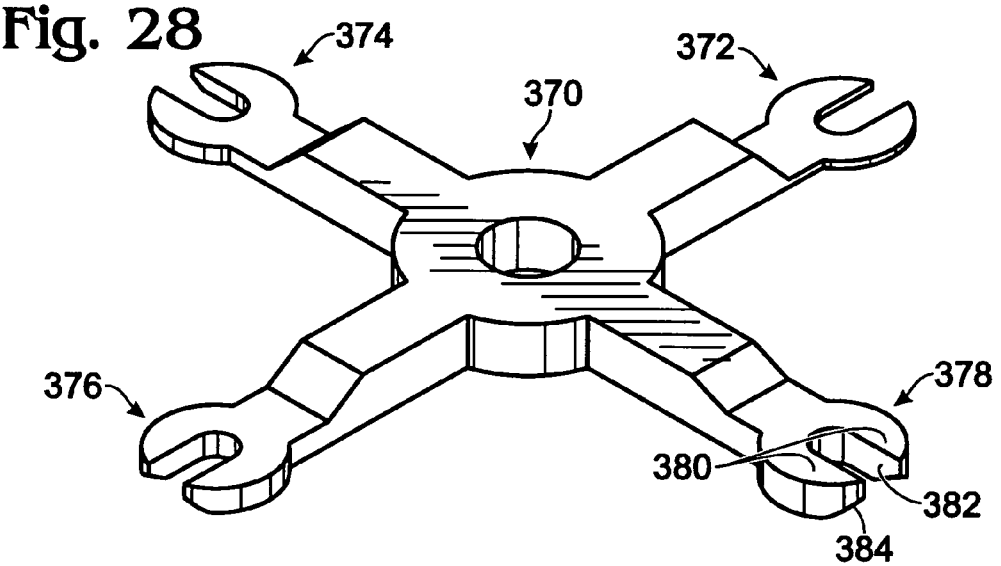
FIG. 28 is a view of a multi-headed spacer tool that may be used with the trial prosthesis of FIG. 24 to adjust and/or measure the head height of the trial prosthesis for selection of a corresponding implant prosthesis from a set of implant prostheses, in accordance with aspects of the present teachings.

FIG. 28 shows a spacer tool 370 that may be used to measure and/or adjust the spacing of the head and stem of the trial prosthesis. The tool may be used to urge the head and stem apart, to restrict approach of the head toward the stem, and/or to measure a spacing of the head from the stem. Tool 370 may include a plurality of spacer elements 372, 374, 376, 378, with a fixed disposition relative to one another. A fixed arrangement of the spacer elements within a single tool may simplify use of the spacer elements. Alternatively, the spacer elements may be included in a plurality of discrete tools, with one or more spacer elements per tool. The thickness of the spacer elements may be different for each spacer element, so that use of each spacer element to adjust the trial prosthesis produces a different head height for the trial prosthesis. Each spacer element may include a pair of fingers 380 separated by an opening 382. Furthermore, the fingers may include a wedge structure (such as bevel 384) that facilitates separation of the head and body components of the trial prosthesis when the spacer element is forced between these components.

FIG. 29 shows the spacer tool in an exemplary position to adjust the head-stem spacing of trial prosthesis 310. The prosthesis may be disposed so that stem 322 is inserted in the canal of radius 390, with shoulder 328 in abutment with radial end 392. Holder 350, which acts as a manipulation tool, may be locked onto collar 326 of the body component. Spacer element 374 may be pushed between head 318 and collar 326 of the trial prosthesis, in a direction shown at 394, so that the thickness of the fingers of the spacer element determines the spacing of the head 318 from collar 326. Bevel 384 may act as a wedge that converts motion of the spacer element in transverse direction 394 into axial movement of the head away from the stem. Alternatively, a spacer element may be positioned between head and body components (spaced more than the thickness of the spacer element), and then these components urged together until they both engage the spacer element.

In some examples, the spacer elements may have thicknesses selected to place the head component at each of the predefined positions determined by the detent mechanism. Accordingly, due to the ability of the detent mechanism to hold the head in position, the spacer element (and holder) can be removed after the spacing has been adjusted, to test motion of the recipient's arm (and the fit of the trial prosthesis) without interference from the spacer element and/or holder.

The systems of the present teachings also or alternatively may include a trial prosthesis with a biased head, such as a "spring-loaded" head. The biased head may be coupled slidably to the stem for axial movement, but may be biased through a biasing mechanism, such as a spring, so that the head is urged away from (or toward) the stem. The trial prosthesis may be installed in place of the natural head of a bone, such as in place of a radial head. The biased head may be urged against the opposing articulation surface by the biasing mechanism (or by one or more spacer elements), so that the head is spaced suitably from the stem, according to the length of missing bone and the recipient's particular anatomy. A distance related to the separation of the stem from the head then may be measured with a measuring device, for example, with the spacer tool described above (or by noting the number and/or size of the spacer elements used to create the spacing). Alternatively, or in addition, the trial prosthesis may include indicia, such as alphanumeric characters, reference marks, colored bands, etc. that indicate the distance. Further aspects of a trial prosthesis with a biasing mechanism are described in the following patent applications, which are incorporated herein by reference: U.S. Provisional Patent Application Ser. No. 60/552,957, filed Mar. 11, 2004; and U.S. Provisional Patent Application Ser. No. 60/571,008, filed May 13, 2004.

Example 7

Selected Embodiments

The following examples describe selected aspects and embodiments of the invention, as a series of indexed paragraphs. These examples are included for illustration and are not intended to limit or define the entire scope of the invention.

1. A prosthesis for replacement of a proximal end of a radius bone, comprising: (A) a body portion including a stem configured to be received in a bore of the radius bone, the stem defining a long axis; and (B) a head portion having a body portion and including a proximal surface tilted at a fixed angle from perpendicular to the long axis.

2. The prosthesis of paragraph 1, wherein the proximal surface defines a tangential plane, and wherein the tangential plane is disposed at the fixed angle.

3. The prosthesis of paragraph 1 or 2, wherein the body portion and the head portion are provided by a body component and a head component that are assembled to mount the head portion on the body portion.

4. The prosthesis of paragraph 3, wherein the body component and the head component define complementary mating structures for engagement in an interference fit.

5. The prosthesis of paragraph 3 or 4, wherein the head component and the body component are configured to be assembled by transverse motion of the head component relative to the body component.

6. The prosthesis of any of paragraphs 3-5, wherein the body component has a proximal end and a threaded opening extending into the body component from the proximal end.

7. The prosthesis of any of paragraphs 3-6, wherein the body component has a collar disposed proximal to the stem, wherein the collar has a proximal surface region, wherein the head component has a distal surface region, and wherein the proximal surface region of the collar and the distal surface region of the head component are configured to form a substantially continuous contour cooperatively when the head component is mounted on the body component.

8. The prosthesis of any of paragraphs 3-7, wherein the body component has a collar disposed proximal to the stem and configured to abut a surface of the radius bone, wherein the collar has a concave profile, wherein the collar has a width measured transverse to the long axis, and wherein the width of the collar is configured to at least substantially match a width of the surface of the radius bone.

9. The prosthesis of any of paragraphs 1-8, wherein the head portion includes an elliptical head, and wherein the elliptical head has a concave proximal surface that is translationally offset from the long axis.

10. The prosthesis of any of paragraphs 1-9, wherein the head portion includes a surface region for articulation with an ulna bone adjacent the radius bone, and wherein the surface region has an at least substantially linear profile and tapers toward the stem.

11. The prosthesis of paragraph 10, wherein the surface region extends more than half way around the head portion.

12. The prosthesis of paragraph 11, wherein the surface region extends about three-fourths of the way around the head portion.

13. The prosthesis of any of paragraphs 10-12, wherein the surface region has a circumferential midpoint and a characteristic dimension measured generally parallel to the long axis, and wherein the characteristic dimension decreases gradually as the surface region extends circumferentially away from the midpoint.

14. The prosthesis of paragraph 1, wherein the head portion is configured for replacement of either a right radial head or a left radial head, but not both.

15. The prosthesis of any of paragraphs 1-14, wherein the head portion includes a side wall defining medial, lateral, anterior, and posterior surface regions, and wherein the proximal surface of the head portion is tilted from perpendicular about an axis generally normal to the medial and lateral surface regions and about another axis generally normal to the anterior and posterior surface regions.

16. The prosthesis of paragraph 15, wherein the proximal surface of the head portion is tilted towards the medial and posterior surface regions.

17. The prosthesis of any of paragraphs 1-16, wherein the proximal surface of the head portion is tilted about 2 to 15 degrees.

18. A kit for replacing an end of a radius bone, comprising: (A) two or more body components, each body component having a stem and an external region fixedly disposed on the stem, the stem defining a long axis and being sized to be received in a bore of the radius bone, the external region being sized to restrict entry of the external region into the bore of the radius bone, each body component including an external region having a different characteristic dimension measured parallel to the long axis; and (B) a head component for articulation with a capitellum of a humerus bone adjacent the radius bone and configured to be assembled with each of the body components individually so that a spacing of the head component from the stem can be varied according to the body component with which the head component is assembled.

19. The kit of paragraph 18, wherein each of the body components is unitary.

20. The kit of paragraph 19, wherein the external region of at least two of the body components includes a collar and a mounting structure for the head component disposed proximal to the collar, wherein the collar has a collar dimension measured parallel to the long axis, and wherein the collar dimension is different for each of the at least two body components.

21. The kit of paragraph 20, wherein at least one of the body components has no collar.

22. The kit of any of paragraphs 18-21, wherein the head component includes a proximal surface that is tilted from perpendicular to the long axis.

23. A kit for replacing an end of a radius bone, comprising: (A) a plurality of body components each having a stem defining a long axis and sized to be received in a bore of the radius bone; and (B) a head component including a head for articulation with a humerus bone and an ulna bone disposed adjacent the radius bone, wherein the head component can be assembled with each of the body components to provide a plurality of prostheses each having a neck disposed between the stem and the head, each neck being formed cooperatively by the head component and one of the body components and creating a different spacing between the head and the stem.

24. A prosthesis for replacement of a proximal end of a radius bone, comprising: (A) a body component including a stem configured to be received in a bore of the radius bone; and (B) a head component configured to be assembled with the body component and including a head for articulation with a humerus bone and an ulna bone adjacent the radius bone, the head component having an anterior surface and an asymmetrical profile when viewed from generally normal to the anterior surface.

25. The prosthesis of paragraph 24, wherein the head component includes opposing proximal and distal ends and an exterior side wall extending between the proximal and distal ends, wherein a medial surface region of the side wall creates a medial portion of the asymmetrical profile, wherein a lateral surface region of the side wall creates a lateral portion of the asymmetrical profile, and wherein the medial and lateral portions of the asymmetrical profile are distinguishable.

26. The prosthesis of paragraph 25, wherein the medial portion is at least substantially linear, and wherein the lateral portion is at least substantially curved.

27. The prosthesis of paragraph 25 or 26, wherein the medial portion is at least substantially convex.

28. The prosthesis of any of paragraphs 25-27, wherein the lateral portion includes a convex proximal region and a concave distal region.

29. The prosthesis of any of paragraphs 25-28, wherein the side wall has a profile that gradually transitions between the medial surface region to the lateral surface region.

30. The prosthesis of any of paragraphs 24-29, wherein the head component has a medial surface and an asymmetrical profile when viewed from generally normal to the medial surface.

31. A method of replacing an end of a radius bone, comprising: (A) selecting a head component for articulation with a capitellum of a humerus bone and a radial notch of an ulna bone adjacent the radius bone; (B) selecting a body component from a set of unitary body components each having a stem sized to be received in a bore of the radius bone and mounting structure disposed to hold the head component at a different spacing from the stem; (C) assembling the head component with the body component; and (D) placing the stem of the body component in the bore of the radius bone.

32. The method of paragraph 31, wherein the step of selecting a head component includes a step of selecting a head component from a set of head components having at least one of different diameters, different lengths, and different angular dispositions after assembly.

33. The method of paragraph 31 or 32, wherein the step of assembling is performed before the step of placing.

34. The method of paragraph 31, further comprising a step of measuring a distance between the radius bone and the capitellum, wherein the step of selecting a body component is based on the step of measuring.

35. The method of paragraph 34, wherein the step of measuring is performed with a trial prosthesis having a stem inserted in the canal and a head contacting the capitellum, wherein the step of measuring includes (1) a step of placing a plurality of spacer elements of different size between the head and the stem and (2) a step of selecting one of the spacer elements, and wherein the step of selecting a body component is based on the step of selecting one of the spacer elements.

36. The method of any of paragraphs 31-35, wherein the head component has an asymmetrical profile, further comprising a step of determining an orientation of the head component relative to surrounding anatomy after the steps of assembling and placing using a fluoroscope to view the asymmetrical profile.

37. A system for selection of a prosthesis to replace an end of a bone, comprising: a trial prosthetic device including (A) a stem configured to be received in a canal of a bone, (B) a head coupled slidably to the stem to adjust a distance between the head and the stem, (C) and a detent mechanism that holds the head selectively at a plurality of predefined distances from the stem.

38. The system of paragraph 37, further comprising one or more spacer tools configured to place the head at one or more of the predefined distances from the stem.

39. The system of paragraph 38, wherein the one or more spacer tools include a plurality of spacer elements, and wherein each spacer element is configured to position the head at a different one of the predefined distances from the stem.

40. The system of any of paragraphs 37-39, further comprising a plurality of spacer elements of different thickness, each spacer element having a wedge structure that converts transverse motion of the spacer element relative to the stem into an increased axial spacing of the stem and head.

41. The system of any of paragraphs 37-40, the stem being a trial stem, the head being a trial head, further comprising a kit providing a plurality of prostheses, each prosthesis having an implant stem and an implant head disposed at a different spacing from the implant stem, wherein each different spacing corresponds to one of the predefined distances.

42. The system of paragraph 41, wherein each head includes a proximal articulation surface, wherein each stem includes a proximal end, wherein each predefined distance and each different spacing is measured from the proximal articulation surface of the head to the proximal end of the stem, and wherein each predefined distance substantially matches one of the different spacings.

43. The system of paragraph 41, wherein the kit includes a head component and a plurality of body components for alternative assembly with the head component to provide the plurality of prostheses.

44. A system for selection of a prosthesis to replace an end of a bone, comprising: (A) a trial prosthetic device including a trial stem configured to be received in a bore of a bone, and a trial head coupled slidably to the trial stem for movement to a plurality of predefined distances from the trial stem; and (B) a kit providing a plurality of prostheses, each prosthesis having an implant stem and an implant head disposed with a different spacing from the implant stem, each different spacing corresponding to one of the predefined distances.

45. The system of paragraph 44, wherein the kit includes a head component and a plurality of body components for alternative assembly with the head component to provide the plurality of prostheses.

46. The system of paragraph 45, wherein the head component mounts by axial motion onto each body component.

47. The system of paragraph 45, wherein the head component is configured to be assembled with each body component at least partially by transverse motion of the head component.

48. The system of any of paragraphs 44-47, wherein the implant stem and the implant head are included in different unitary components.

49. The system of any of paragraph 44-48, further comprising a plurality of spacer elements, each spacer element configured to define and/or measure a separation between the trial head and trial stem corresponding to a different one of the predefined distances.

50. The system of paragraph 49, wherein one or more of the spacer elements include wedge structure configured to convert transverse motion of the spacer element into increased axial separation of the trial head and the trial stem.

51. A method of selecting a prosthesis to replace an end of a bone, comprising: (A) installing a trial prosthetic device by inserting a trial stem in a bore of the bone, the trial prosthetic device including a trial head coupled slidably to the trial stem for movement to a plurality of predefined distances from the trial stem; (B) individually placing a plurality of spacer elements of different thickness between the trial head and the trial stem to position the trial head at each of the predefined distances; (C) selecting a spacer element from the plurality of spacer elements after the step of placing; and (D) selecting a prosthesis from a set of available prostheses based on the step of selecting a spacer element.

52. The method of paragraph 51, the trial stem being included in a body component, wherein the step of placing includes a step of wedging one or more of the spacer elements individually between the trial head and the body component.

53. The method of paragraph 51 or 52, wherein the set of available prostheses is formed by pairwise assembly of at least one head component with a plurality of body components or of a plurality of head components with at least one body component, and wherein each of the plurality of spacer elements corresponds to a different head component or body component.

The disclosure set forth above may encompass multiple distinct inventions with independent utility. Although each of these inventions has been disclosed in its preferred form(s), the specific embodiments thereof as disclosed and illustrated herein are not to be considered in a limiting sense, because numerous variations are possible. The subject matter of the inventions includes all novel and nonobvious combinations and subcombinations of the various elements, features, functions, and/or properties disclosed herein. The following claims particularly point out certain combinations and subcombinations regarded as novel and nonobvious. Inventions embodied in other combinations and subcombinations of features, functions, elements, and/or properties may be claimed in applications claiming priority from this or a related application. Such claims, whether directed to a different invention or to the same invention, and whether broader, narrower, equal, or different in scope to the original claims, also are regarded as included within the subject matter of the inventions of the present disclosure.

We claim:

1. A device for replacement of a proximal end of a radius bone in an elbow joint, comprising:
    an elbow prosthesis including
        a body portion including a stem configured to be received in a bore of a radius bone, the stem defining a longitudinal axis; and
        a radial head portion having a shape corresponding to a proximal head of a radius bone to permit articulation of the head portion with a humerus bone and an ulna bone adjacent the radius bone in an elbow joint, the head portion being mounted on the body portion and including a side wall defining medial, lateral, anterior, and posterior surface regions and also including a concave proximal articulation surface defining a proximal plane that is tilted towards the medial and posterior surface regions at a fixed angle from perpendicular to the longitudinal axis, the fixed angle being defined by manufacture of the body and head portions,
        wherein the head portion is elongated along a first head axis that is orthogonal to the longitudinal axis, wherein a second head axis is coplanar with the first head axis and orthogonal to both the longitudinal axis and the first head axis, and wherein the proximal plane intersects a plane containing the first and second head axes to define a line that is oblique to the first and second head axes, therefore the head portion being bilaterally asymmetrical such that the head portion is configured to replace either a right radial head or a left radial head, but not both, and
        wherein the body portion and the head portion are provided by a body component and a head component that are discrete from one another.

2. The device of claim 1, wherein the proximal plane is tilted about 2 to 15 degrees from perpendicular to the longitudinal axis.

3. The device of claim 1, wherein the body component has a collar disposed proximally to the stem, and wherein a distal end of the head component and a proximal end of the collar have about the same diameter to form a substantially continuous contour cooperatively when the head component is mounted on the body component.

4. The device of claim 1, wherein the body component has a collar disposed proximally to the stem and configured to abut a surface of the radius bone, wherein the collar has a concave profile and flares away from the stem, wherein the collar has a width measured transversely to the longitudinal axis, and wherein the width of the collar is configured to at least substantially match a diameter of the radius bone measured at the surface of the radius bone that is abutted.

5. The device of claim 1, wherein the head component includes a surface region configured to articulate with an ulna bone adjacent the radius bone, and wherein the surface region configured to articulate with an ulna bone has an at least substantially linear profile and tapers toward the stem.

6. The device of claim 1, wherein the medial surface region creates a medial profile, wherein the lateral surface region creates a lateral profile, wherein the medial and lateral profiles are asymmetrical with respect to each other, and wherein the lateral profile includes a convex proximal region and a concave distal region.

7. The device of claim 6, wherein the lateral profile is more curved than the medial profile.

8. The device of claim 6, wherein the medial profile is at least substantially convex.

9. A device for replacement of a proximal end of a radius bone in an elbow joint, comprising:
   an elbow prosthesis including
      a body portion including a stem configured to be received in a bore of a radius bone, the stem defining a longitudinal axis; and
      a radial head portion having a shape corresponding to a proximal head of a radius bone to permit articulation of the head portion with a humerus bone and an ulna bone adjacent the radius bone in an elbow joint, the head portion being mounted on the body portion and including a side wall defining medial, lateral, anterior, and posterior surface regions and also including a concave proximal articulation surface defining a proximal plane that is tilted towards the medial and posterior surface regions at a fixed angle from perpendicular to the longitudinal axis, the fixed angle being defined by manufacture of the body and head portions,
      wherein the head portion includes a reference mark formed on the lateral surface region, wherein a first head axis is orthogonal to the longitudinal axis and intersects the longitudinal axis and the reference mark, wherein a second head axis is coplanar with the first head axis and orthogonal to both the first head axis and the longitudinal axis, and wherein the proximal plane intersects a plane containing the first and second head axes to define a line that is oblique to the first and second head axes, therefore the head portion being bilaterally asymmetrical such that the head portion is configured to replace either a right radial head or a left radial head, but not both, and
      wherein the body portion and the head portion are provided by a body component and a head component that are discrete from one another.

10. The device of claim 9, wherein the head portion is elliptical.

11. The device of claim 9, wherein the proximal plane is tilted about 2 to 15 degrees from perpendicular to the longitudinal axis.

12. The device of claim 9, wherein the body component has a collar disposed proximally to the stem, and wherein a distal end of the head component and a proximal end of the collar have about the same diameter to form a substantially continuous contour cooperatively when the head component is mounted on the body component.

13. The device of claim 9, wherein the head component includes a surface region configured to articulate with an ulna bone adjacent the radius bone, and wherein the surface region configured to articulate with an ulna bone has an at least substantially linear profile and tapers toward the stem.

* * * * *